US012642542B1

(12) United States Patent
Gamez et al.

(10) Patent No.: US 12,642,542 B1
(45) Date of Patent: *Jun. 2, 2026

(54) ADAPTIVE PRESSURE-CYCLICAL ASPIRATION DEVICE AND METHODS

(71) Applicant: Von Vascular, Inc., Sunrise, FL (US)

(72) Inventors: Victor Gamez, Miramar, FL (US); Manning J. Hanser, Weston, FL (US); Alfonso Hermida, Miramar, FL (US)

(73) Assignee: Von Vascular, Inc., Weston, FL (US)

( * ) Notice: Subject to any disclaimer, the term of this patent is extended or adjusted under 35 U.S.C. 154(b) by 472 days.

This patent is subject to a terminal disclaimer.

(21) Appl. No.: 18/123,973

(22) Filed: Mar. 20, 2023

Related U.S. Application Data

(60) Provisional application No. 63/474,167, filed on Jul. 26, 2022, provisional application No. 63/335,168, filed on Apr. 26, 2022, provisional application No. 63/325,778, filed on Mar. 31, 2022, provisional application No. 63/321,706, filed on Mar. 20, 2022.

(51) Int. Cl.
| | |
|---|---|
| *A61B 17/22* | (2006.01) |
| *A61M 1/00* | (2006.01) |
| *A61B 17/00* | (2006.01) |

(52) U.S. Cl.
CPC .............. *A61B 17/22* (2013.01); *A61M 1/74* (2021.05); *A61B 2017/00022* (2013.01); *A61B 2017/00199* (2013.01); *A61B 2017/22079* (2013.01)

(58) Field of Classification Search
CPC .............. A61B 17/22; A61B 17/00234; A61B 2017/00022; A61B 2017/00123; A61B 2017/00137; A61B 2017/00199; A61B 2017/00292; A61B 2017/00561; A61B 2017/00778; A61B 2017/22079
See application file for complete search history.

(56) References Cited

U.S. PATENT DOCUMENTS

| | | | |
|---|---|---|---|
| 3,589,363 A | 6/1971 | Banko et al. | |
| 3,955,574 A | 5/1976 | Rubensten | |
| 4,798,580 A | 1/1989 | DeMeo et al. | |
| | (Continued) | | |

FOREIGN PATENT DOCUMENTS

| | | |
|---|---|---|
| CN | 118251244 A | 6/2024 |
| EP | 0777504 B1 | 10/1998 |
| | (Continued) | |

OTHER PUBLICATIONS

Mathews, S. Jay et al. "The Akura Thrombectomy Catheter System for the Treatment of VTE," Insert to Endovascular Today, vol. 23, No. 1, Jan. 2024 (4 pages).

(Continued)

*Primary Examiner* — Katherine M Rodjom

(57) ABSTRACT

An aspiration system operable for relieving occlusions caused by clots and other lodged bodies in a vessel uses a cyclic algorithm which is adaptable to receipt of any known or developed aspiration catheter to treat acute ischemic occlusions by applied alternating catheter pressure within a defined range. The application of the algorithm is customizable by the specific physical characteristics of the catheter selected, making the system universally applicable to a significant range of catheters. A user interface may be provided conveniently within reach of the user enabling interactive input of intervening selections based on recommendations by a processor running the algorithm.

17 Claims, 22 Drawing Sheets

(56)                    References Cited

U.S. PATENT DOCUMENTS

| | | | |
|---|---|---|---|
| 4,832,685 A | 5/1989 | Haines | |
| 4,921,477 A | 5/1990 | Davis | |
| 4,930,997 A | 6/1990 | Bennett | |
| 4,935,005 A | 6/1990 | Haines | |
| 5,125,891 A | 6/1992 | Hossain et al. | |
| 5,256,233 A | 10/1993 | Winter et al. | |
| 5,267,956 A | 12/1993 | Beuchat | |
| 5,364,342 A | 11/1994 | Beuchat | |
| 5,419,774 A | 5/1995 | Willard et al. | |
| 5,454,795 A | 10/1995 | Samson | |
| 5,460,490 A | 10/1995 | Carr et al. | |
| 5,496,270 A | 3/1996 | Nettekoven | |
| 5,827,229 A | 10/1998 | Auth et al. | |
| 5,938,587 A | 8/1999 | Taylor et al. | |
| 6,022,747 A | 2/2000 | Gherson et al. | |
| 6,071,267 A | 6/2000 | Zamierowski | |
| 6,115,860 A | 9/2000 | Vrzalik | |
| D445,804 S | 7/2001 | Tsai | |
| 6,306,163 B1 | 10/2001 | Fitz | |
| 6,387,065 B1 | 5/2002 | Tumey | |
| 6,468,237 B1 | 10/2002 | Lina | |
| 6,517,513 B1 | 2/2003 | Covington | |
| 6,547,756 B1 | 4/2003 | Greter et al. | |
| 6,673,028 B1 | 1/2004 | Argenta et al. | |
| 6,858,024 B1 | 2/2005 | Berg et al. | |
| 6,904,631 B2 | 6/2005 | Vrzalik et al. | |
| 6,942,634 B2 | 9/2005 | Odland | |
| 7,004,915 B2 | 2/2006 | Boynton et al. | |
| D520,023 S | 5/2006 | Goto et al. | |
| 7,108,683 B2 | 9/2006 | Zamierowski | |
| 7,198,046 B1 | 4/2007 | Argenta et al. | |
| 7,276,052 B2 | 10/2007 | Kobayashi et al. | |
| 7,284,965 B2 | 10/2007 | Adahan | |
| D573,609 S | 7/2008 | Bilger | |
| 7,410,491 B2 | 8/2008 | Hopkins et al. | |
| 7,618,382 B2 | 11/2009 | Vogel et al. | |
| 7,662,109 B2 | 2/2010 | Hibner | |
| 7,666,161 B2 | 2/2010 | Nash et al. | |
| 7,713,235 B2 | 5/2010 | Torrance et al. | |
| 7,717,853 B2 | 5/2010 | Nita | |
| 7,828,748 B2 | 11/2010 | Hibner | |
| 7,842,009 B2 | 11/2010 | Torrance et al. | |
| 7,854,707 B2 | 12/2010 | Hibner et al. | |
| 7,867,173 B2 | 1/2011 | Hibner et al. | |
| 7,896,817 B2 | 3/2011 | Garrison | |
| 7,918,804 B2 | 4/2011 | Monson et al. | |
| 7,918,822 B2 | 4/2011 | Kumar et al. | |
| 7,931,659 B2 | 4/2011 | Bose et al. | |
| 7,938,786 B2 | 5/2011 | Ritchie et al. | |
| 7,959,608 B2 | 6/2011 | Nash et al. | |
| 7,981,049 B2 | 7/2011 | Ritchie et al. | |
| 8,038,627 B2 | 10/2011 | Hibner | |
| 8,070,735 B2 | 12/2011 | Koch et al. | |
| 8,075,510 B2 | 12/2011 | Aklog et al. | |
| 8,118,755 B2 | 2/2012 | Hibner et al. | |
| 8,235,955 B2 | 8/2012 | Blott et al. | |
| 8,251,916 B2 | 8/2012 | Speeg et al. | |
| 8,333,796 B2 | 12/2012 | Tompkins | |
| 8,337,475 B2 | 12/2012 | Christensen et al. | |
| 8,366,735 B2 | 2/2013 | Bose et al. | |
| 8,394,078 B2 | 3/2013 | Torrance et al. | |
| 8,414,534 B2 | 4/2013 | Bandhauer et al. | |
| 8,460,312 B2 | 6/2013 | Bose et al. | |
| 8,465,467 B2 | 6/2013 | Gao | |
| 8,480,595 B2 | 7/2013 | Speeg et al. | |
| 8,506,512 B2 | 8/2013 | Aklog et al. | |
| 8,591,453 B2 | 11/2013 | Stubkjaer et al. | |
| 8,613,717 B2 | 12/2013 | Aklog et al. | |
| 8,632,498 B2 | 1/2014 | Rimsa et al. | |
| 8,657,785 B2 | 2/2014 | Torrance et al. | |
| 8,679,150 B1 | 3/2014 | Janardhan et al. | |
| 8,690,907 B1 | 4/2014 | Janardhan et al. | |
| 8,702,623 B2 | 4/2014 | Parihar et al. | |
| 8,715,314 B1 | 5/2014 | Janardhan et al. | |
| 8,715,315 B1 | 5/2014 | Janardhan et al. | |
| 8,715,316 B1 | 5/2014 | Janardhan et al. | |
| 8,721,676 B1 | 5/2014 | Janardhan et al. | |
| 8,721,677 B1 | 5/2014 | Janardhan et al. | |
| 8,733,618 B1 | 5/2014 | Janardhan et al. | |
| 8,734,374 B2 | 5/2014 | Aklog et al. | |
| 8,737,017 B1 | 5/2014 | Abe | |
| 8,747,432 B1 | 6/2014 | Janardhan et al. | |
| 8,753,371 B1 | 6/2014 | Janardhan et al. | |
| 8,758,315 B2 | 6/2014 | Chen et al. | |
| 8,783,151 B1 | 7/2014 | Janardhan et al. | |
| 8,789,452 B1 | 7/2014 | Janardhan et al. | |
| 8,795,244 B2 | 8/2014 | Randolph et al. | |
| 8,803,030 B1 | 8/2014 | Janardhan et al. | |
| 8,816,247 B1 | 8/2014 | Janardhan et al. | |
| D712,933 S | 9/2014 | DeOreo et al. | |
| 8,852,219 B2 | 10/2014 | Wulfman et al. | |
| 8,852,227 B1 | 10/2014 | Janardhan et al. | |
| 8,859,934 B1 | 10/2014 | Janardhan et al. | |
| 8,872,068 B1 | 10/2014 | Janardhan et al. | |
| 8,882,797 B2 | 11/2014 | Janardhan et al. | |
| 8,895,891 B2 | 11/2014 | Janardhan et al. | |
| 8,904,914 B2 | 12/2014 | Janardhan et al. | |
| 8,910,555 B2 | 12/2014 | Janardhan et al. | |
| 8,911,487 B2 | 12/2014 | Bennett | |
| 8,920,402 B2 | 12/2014 | Nash et al. | |
| 8,932,320 B1 | 1/2015 | Janardhan et al. | |
| 9,034,007 B2 | 5/2015 | Janardhan | |
| 9,078,964 B2 | 7/2015 | Schuman | |
| 9,095,326 B2 | 8/2015 | Ritchie et al. | |
| 9,119,656 B2 | 9/2015 | Bose et al. | |
| 9,125,731 B2 | 9/2015 | Ross et al. | |
| 9,179,931 B2 | 11/2015 | Janardhan et al. | |
| 9,179,995 B2 | 11/2015 | Janardhan et al. | |
| 9,186,444 B2 | 11/2015 | Lonky et al. | |
| 9,241,699 B1 | 1/2016 | Kume et al. | |
| 9,265,512 B2 | 2/2016 | Garrison et al. | |
| 9,314,324 B2 | 4/2016 | Janardhan et al. | |
| 9,332,998 B2 | 5/2016 | Ray et al. | |
| 9,332,999 B2 | 5/2016 | Ray et al. | |
| 9,345,457 B2 | 5/2016 | Speeg et al. | |
| 9,402,938 B2 | 8/2016 | Aklog et al. | |
| RE46,135 E | 9/2016 | Hibner | |
| 9,445,831 B2 | 9/2016 | Mark | |
| 9,526,865 B2 | 12/2016 | Quick | |
| 9,532,792 B2 | 1/2017 | Galdonik et al. | |
| 9,561,129 B2 | 2/2017 | Ross et al. | |
| 9,561,345 B2 | 2/2017 | Garrison et al. | |
| 9,592,068 B2 | 3/2017 | Janardhan et al. | |
| 9,615,832 B2 | 4/2017 | Bose et al. | |
| 9,655,633 B2 | 5/2017 | Leynov et al. | |
| 9,693,789 B2 | 7/2017 | Garrison et al. | |
| 9,750,524 B2 | 9/2017 | Janardhan et al. | |
| 9,820,761 B2 | 11/2017 | Garrison et al. | |
| 9,833,251 B2 | 12/2017 | Janardhan et al. | |
| 9,855,374 B2 | 1/2018 | Sherman et al. | |
| 9,883,854 B2 | 2/2018 | Mak | |
| 9,883,877 B2 | 2/2018 | Look et al. | |
| 9,901,435 B2 | 2/2018 | Janardhan et al. | |
| 9,915,674 B2 | 3/2018 | Zordan | |
| 9,943,321 B2 | 4/2018 | Nita | |
| 9,956,326 B2 | 5/2018 | Ramella et al. | |
| 9,999,710 B2 | 6/2018 | Ross et al. | |
| 10,219,814 B2 | 3/2019 | Feltyberger et al. | |
| 10,238,789 B2 | 3/2019 | Kuntz et al. | |
| 10,251,739 B2 | 4/2019 | Janardhan et al. | |
| D847,864 S | 5/2019 | Janardhan et al. | |
| D847,865 S | 5/2019 | Janardhan et al. | |
| D847,866 S | 5/2019 | Janardhan et al. | |
| D850,490 S | 6/2019 | Janardhan et al. | |
| 10,335,260 B2 | 7/2019 | Janardhan et al. | |
| 10,342,655 B2 | 7/2019 | Janardhan et al. | |
| 10,390,926 B2 | 8/2019 | Janardhan et al. | |
| 10,463,468 B2 | 11/2019 | Janardhan et al. | |
| 10,517,617 B2 | 12/2019 | Aklog et al. | |
| 10,531,883 B1 | 1/2020 | Deville et al. | |
| 10,722,253 B2 | 7/2020 | Deville et al. | |
| 10,751,159 B2 | 8/2020 | Janardhan et al. | |
| D896,847 S | 9/2020 | Janardhan et al. | |
| 10,799,669 B2 | 10/2020 | Chou et al. | |

(56)                    References Cited

U.S. PATENT DOCUMENTS

| | | |
|---|---|---|
| 10,946,123 B2 | 3/2021 | Christensen et al. |
| 11,020,133 B2 | 6/2021 | Wilson et al. |
| 11,052,006 B2 | 7/2021 | Tanaka |
| 11,065,019 B1 | 7/2021 | Chou et al. |
| 11,071,812 B2 | 7/2021 | Raman et al. |
| 11,096,703 B2 | 8/2021 | Panian |
| 11,096,712 B2 | 8/2021 | Teigen et al. |
| 11,147,949 B2 | 10/2021 | Yang et al. |
| 11,197,683 B1 | 12/2021 | Teigen et al. |
| 11,197,977 B2 | 12/2021 | Mullins et al. |
| 11,298,144 B2 | 4/2022 | Janardhan et al. |
| 11,337,712 B2 | 5/2022 | Teigen et al. |
| 11,337,855 B2 | 5/2022 | Bandhauer et al. |
| 11,399,861 B2 | 8/2022 | Stulen et al. |
| 11,400,255 B1 | 8/2022 | Chou et al. |
| 11,406,402 B2 | 8/2022 | Deville et al. |
| 11,432,835 B2 | 9/2022 | Shaffer et al. |
| 11,436,806 B1 | 9/2022 | Katz et al. |
| 11,490,911 B2 | 11/2022 | Panian |
| 11,497,523 B2 | 11/2022 | Trosper et al. |
| 11,523,830 B2 | 12/2022 | Tompkins et al. |
| 11,547,426 B2 | 1/2023 | Deville et al. |
| 11,553,935 B2 | 1/2023 | Buck et al. |
| 11,586,276 B2 | 2/2023 | Winold et al. |
| 11,638,660 B2 | 5/2023 | Balkenbush et al. |
| 11,730,499 B1 | 8/2023 | Thio et al. |
| 11,744,600 B2 | 9/2023 | Look et al. |
| 11,759,219 B2 | 9/2023 | Teigen et al. |
| 11,844,891 B2 | 12/2023 | Hanani et al. |
| 11,890,024 B2 | 2/2024 | Panian |
| 11,918,240 B2 | 3/2024 | Deville et al. |
| 12,005,228 B2 | 6/2024 | Ofek et al. |
| 12,076,225 B2 | 9/2024 | Erbey et al. |
| 12,201,311 B2 | 1/2025 | Teigen et al. |
| 12,208,196 B2 | 1/2025 | Quintanar |
| 12,251,119 B2 | 3/2025 | Naglreiter et al. |
| 2003/0069549 A1 | 4/2003 | MacMahon et al. |
| 2005/0085769 A1 | 4/2005 | MacMahon et al. |
| 2005/0124969 A1 | 6/2005 | Fitzgerald et al. |
| 2006/0058837 A1 | 3/2006 | Bose et al. |
| 2007/0038100 A1 | 2/2007 | Nita |
| 2007/0135832 A1 | 6/2007 | Wholey et al. |
| 2007/0166180 A1 | 7/2007 | Adahan |
| 2007/0239261 A1 | 10/2007 | Bose et al. |
| 2007/0269321 A1 | 11/2007 | Adahan |
| 2008/0004545 A1 | 1/2008 | Garrison |
| 2008/0015478 A1 | 1/2008 | Bose |
| 2008/0051708 A1 | 2/2008 | Kumar et al. |
| 2008/0056915 A1 | 3/2008 | Adahan |
| 2008/0319355 A1 | 12/2008 | Nita |
| 2009/0005747 A1 | 1/2009 | Michaels et al. |
| 2009/0030400 A1 | 1/2009 | Bose et al. |
| 2009/0187131 A1 | 7/2009 | Fitzgerald et al. |
| 2009/0318892 A1 | 12/2009 | Aboytes et al. |
| 2010/0114017 A1 | 5/2010 | Lenker et al. |
| 2010/0150991 A1 | 6/2010 | Bernstein |
| 2010/0191178 A1 | 7/2010 | Ross et al. |
| 2010/0204672 A1 | 8/2010 | Lockhart et al. |
| 2010/0217276 A1 | 8/2010 | Garrison et al. |
| 2010/0280434 A1 | 11/2010 | Raney et al. |
| 2011/0137231 A1 | 6/2011 | Sorensen et al. |
| 2011/0160621 A1 | 6/2011 | Nita |
| 2011/0160761 A1 | 6/2011 | Ferrera et al. |
| 2011/0184454 A1 | 7/2011 | Barry et al. |
| 2011/0213290 A1 | 9/2011 | Chin et al. |
| 2011/0213392 A1 | 9/2011 | Aklog et al. |
| 2011/0264133 A1 | 10/2011 | Hanlon et al. |
| 2011/0313328 A1 | 12/2011 | Nita |
| 2011/0319927 A1 | 12/2011 | Nita |
| 2012/0078140 A1 | 3/2012 | Nita |
| 2012/0078285 A1 | 3/2012 | Griffin |
| 2012/0150147 A1 | 6/2012 | Leynov et al. |
| 2012/0283563 A1 | 11/2012 | Moore et al. |
| 2012/0330196 A1 | 12/2012 | Nita |
| 2013/0304082 A1 | 11/2013 | Aklog et al. |
| 2013/0324882 A1 | 12/2013 | Mescher |
| 2014/0039343 A1 | 2/2014 | Mescher et al. |
| 2014/0128907 A1 | 5/2014 | Hui et al. |
| 2014/0180377 A1 | 6/2014 | Bose et al. |
| 2014/0271273 A1 | 9/2014 | Carpenter |
| 2014/0276897 A1 | 9/2014 | Rockley et al. |
| 2014/0277082 A1 | 9/2014 | Janardhan et al. |
| 2015/0028005 A1 | 1/2015 | Janardhan et al. |
| 2015/0032121 A1 | 1/2015 | Janardhan et al. |
| 2015/0032146 A1 | 1/2015 | Janardhan et al. |
| 2015/0032147 A1 | 1/2015 | Janardhan et al. |
| 2015/0196304 A1 | 7/2015 | Rabkin et al. |
| 2015/0238303 A1 | 8/2015 | Janardhan |
| 2015/0359666 A1 | 12/2015 | Zacharias |
| 2016/0058614 A1 | 3/2016 | Ross et al. |
| 2016/0120557 A1 | 5/2016 | Goddard et al. |
| 2016/0166265 A1 | 6/2016 | Nita |
| 2017/0021072 A1 | 1/2017 | Forsell |
| 2017/0105743 A1 | 4/2017 | Vale et al. |
| 2017/0112981 A1 | 4/2017 | Friedman et al. |
| 2017/0136158 A1 | 5/2017 | Culhane et al. |
| 2017/0147765 A1 | 5/2017 | Mehta |
| 2017/0151032 A1 | 6/2017 | Loisel |
| 2017/0165001 A1 | 6/2017 | Lyttle |
| 2017/0181760 A1 | 6/2017 | Look et al. |
| 2017/0181761 A1 | 6/2017 | Janardhan et al. |
| 2017/0333060 A1 | 11/2017 | Panian |
| 2017/0360469 A1 | 12/2017 | Janardhan et al. |
| 2018/0049921 A1 | 2/2018 | Sorensen et al. |
| 2018/0085136 A1 | 3/2018 | Janardhan et al. |
| 2018/0197633 A1 | 7/2018 | Mehta |
| 2018/0228502 A1 | 8/2018 | Shaffer et al. |
| 2018/0256797 A1 | 9/2018 | Schenck et al. |
| 2018/0263646 A1 | 9/2018 | Loisel |
| 2018/0338770 A1 | 11/2018 | Mogi et al. |
| 2018/0339130 A1 | 11/2018 | Ogle |
| 2019/0133745 A1 | 5/2019 | Janardhan et al. |
| 2019/0142567 A1 | 5/2019 | Janardhan et al. |
| 2019/0142568 A1 | 5/2019 | Janardhan et al. |
| 2019/0167406 A1 | 6/2019 | Janardhan et al. |
| 2020/0046368 A1 | 2/2020 | Merritt et al. |
| 2020/0297362 A1 | 9/2020 | Deville et al. |
| 2020/0397956 A1 | 12/2020 | Luxon et al. |
| 2020/0397957 A1 | 12/2020 | Teigen et al. |
| 2021/0093344 A1 | 4/2021 | Janardhan et al. |
| 2021/0137540 A1 | 5/2021 | Panian |
| 2021/0186534 A1 | 6/2021 | Hunt et al. |
| 2021/0378691 A1 | 12/2021 | Panian |
| 2022/0054151 A1 | 2/2022 | Shifflette |
| 2022/0168000 A1 | 6/2022 | Naglreiter et al. |
| 2022/0168001 A1 | 6/2022 | Naglreiter et al. |
| 2022/0168002 A1 | 6/2022 | Naglreiter et al. |
| 2022/0280171 A1 | 9/2022 | Teigen et al. |
| 2022/0296260 A1 | 9/2022 | Janardhan et al. |
| 2022/0296261 A1 | 9/2022 | Panian |
| 2022/0313288 A1 | 10/2022 | Janardhan et al. |
| 2022/0323096 A1 | 10/2022 | Naglreiter |
| 2022/0330958 A1 | 10/2022 | Mobley |
| 2022/0378449 A1 | 12/2022 | Look et al. |
| 2023/0000510 A1 | 1/2023 | Brady et al. |
| 2023/0026412 A1 | 1/2023 | Teigen et al. |
| 2023/0043096 A1 | 2/2023 | Panian |
| 2023/0063577 A1 | 3/2023 | Pons |
| 2023/0099283 A1 | 3/2023 | Deville et al. |
| 2023/0100426 A1 | 3/2023 | Deville et al. |
| 2023/0112635 A1 | 4/2023 | Panian |
| 2023/0181200 A1 | 6/2023 | Deville et al. |
| 2023/0240694 A1 | 8/2023 | Panian |
| 2023/0263545 A1 | 8/2023 | Wilcox et al. |
| 2023/0364319 A1 | 11/2023 | Vale et al. |
| 2024/0000469 A1 | 1/2024 | Teigen et al. |
| 2024/0138858 A1 | 5/2024 | Gamez et al. |
| 2024/0148957 A1 | 5/2024 | Brown et al. |
| 2024/0148958 A1 | 5/2024 | Reyes et al. |
| 2024/0277914 A1 | 8/2024 | Vale et al. |
| 2024/0285292 A1 | 8/2024 | Hanser et al. |
| 2025/0064466 A1 | 2/2025 | Hanser et al. |

(56)                    References Cited

U.S. PATENT DOCUMENTS

| | | |
|---|---|---|
| 2025/0064467 A1 | 2/2025 | Hanser et al. |
| 2025/0288306 A1 | 9/2025 | Hanser et al. |

FOREIGN PATENT DOCUMENTS

| | | | |
|---|---|---|---|
| EP | 3123964 B1 | 4/2019 |
| WO | WO 2006/117207 A1 | 11/2006 |
| WO | WO 2012/057881 A1 | 5/2012 |
| WO | WO 2014/151209 A1 | 9/2014 |
| WO | WO 2015/157330 A1 | 10/2015 |
| WO | WO 2016/018448 A1 | 2/2016 |
| WO | WO 2017/134462 A1 | 8/2017 |
| WO | WO 2021/108371 | 6/2021 |
| WO | WO 2023/220633 A2 | 11/2023 |
| WO | WO 2024/016004 A2 | 1/2024 |

OTHER PUBLICATIONS

Baek, Hong-Gyu et al. "Craniotomy and Membranectomy for Treatment of Organized Chronic Subdural Hematoma," Korean Journal of Neurotrauma, 2018 (12 pages).

Lee, Kyeong-Seok et al. "Acute-on-Chronic Subdural Hematoma: Not Uncommon Events," Journal of Korean Neurosurgical Society, 2011 (13 pages).

Majovsky, Martin et al. "Burr-Hole Evacuation of Chronic Subdural Hematoma: Biophysically and Evidence-Based Technique Improvement," Journal of Neurosciences in Rural Practice, 2018 (6 pages).

Manivannan, Susruta et al. "Acute subdural haematoma in the elderly: to operate or not to operate? A systematic review and meta-analysis of outcomes following surgery," BMJ Open, 2021 (13 pages).

Peng, Deqing et al. "External drains versus No. drains after burr-hole evacuation for the treatment of chronic subdural haematoma in adults," Cochrane Database of Systematic Reviews, Chochrane Library, Aug. 31, 2016 (56 pages).

Xu, Min et al. "Minimally Invasive Surgery in Chronic Subdural Hematoma: Prognosis and Recurrence Factors of 516 Cases in a Single Center," Journal of Clinical Medicine, 2022 (8 pages).

International Search Report and Written Opinion for PCT/US2024/015950, mailed Aug. 7, 2024.

Office Action for U.S. Appl. No. 18/596,868, mailed Sep. 10, 2024.

Office Action for U.S. Appl. No. 18/949,280, mailed Dec. 16, 2024.

Office Action for U.S. Appl. No. 19/223,433, mailed Aug. 6, 2025.

Office Action for U.S. Appl. No. 18/373,955, mailed Oct. 2, 2025.

International Search Report and Written Opinion for PCT/US2025/037893, mailed Oct. 28, 2025.

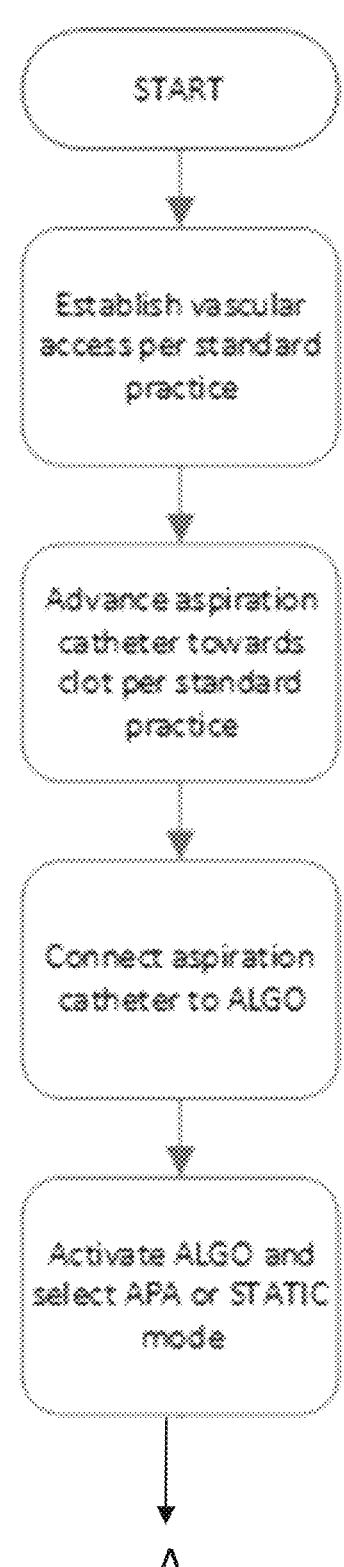
FIG. 7A    A

FIG. 17A

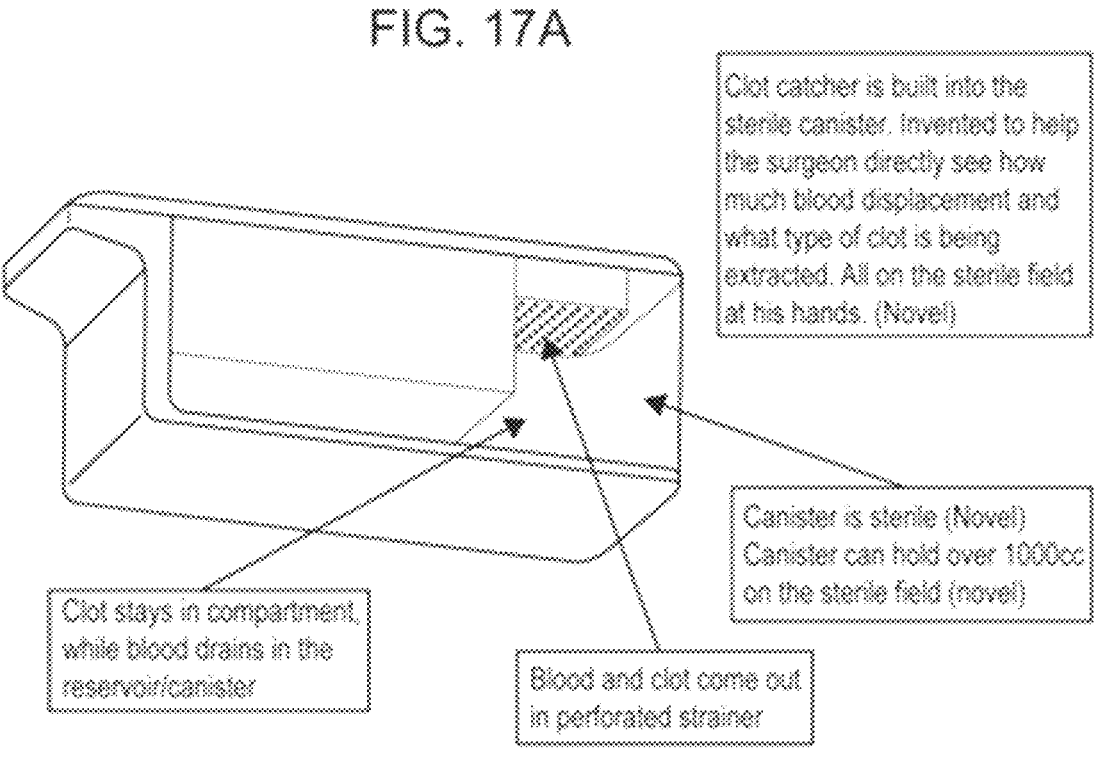

Clot catcher is built into the sterile canister. Invented to help the surgeon directly see how much blood displacement and what type of clot is being extracted. All on the sterile field at his hands. (Novel)

Canister is sterile (Novel) Canister can hold over 1000cc on the sterile field (novel)

Clot stays in compartment, while blood drains in the reservoir/canister

Blood and clot come out in perforated strainer

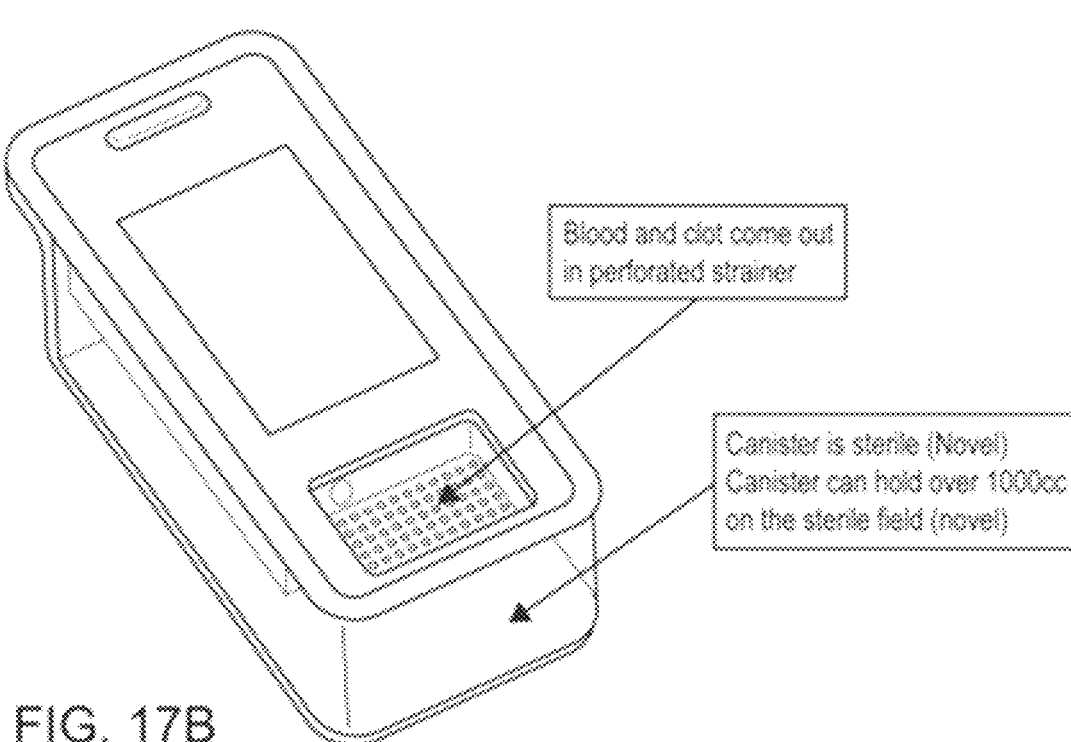

Blood and clot come out in perforated strainer

Canister is sterile (Novel) Canister can hold over 1000cc on the sterile field (novel)

FIG. 17B

ADAPTIVE PRESSURE-CYCLICAL ASPIRATION DEVICE AND METHODS

CROSS REFERENCE TO RELATED APPLICATIONS

This application claims the benefit of U.S. Provisional Application No. 63/321,706 filed Mar. 20, 2023 entitled NOVEL ENHANCED ACUTE ISCHEMIC STROKE ASPIRATION ENERGY SOURCE, U.S. Provisional Application No. 63/325,778 filed Mar. 31, 2022 entitled NOVEL ENHANCED ACUTE ISCHEMIC STROKE ASPIRATION SOURCE, U.S. Provisional Application No. 63/335, 168 filed Apr. 26, 2022 entitled NOVEL ENHANCED ASPIRATION SOURCE, and U.S. Provisional Application No. 63/474,167 filed Jul. 26, 2022 entitled ALGORITHMS FOR NOVEL ENHANCED ASPIRATION SOURCE.

BACKGROUND OF THE INVENTION

The present disclosures relate, inter alia, to improved acute ischemic event therapies, and equipment and methods for implementing same to effectively and efficiently remove a clot occluding a vessel.

Conventional thrombotic extraction strategies for removing a clot occluding a blood vessel have routinely applied static aspiration. Attendant with such approach, plugging of a clot-extraction catheter had been heretofore encountered, thereby rendering continued use of the catheter essentially ineffective.

For example, when trying to aspirate a clot that is larger than the catheter, the clot often plugs the catheter according to a static aspiration approach. In particular, the clot is pulled partially into the catheter along a length thereof. The longer this length, the greater the friction there is present between the clot and the ID of the catheter. When the applied vacuum is alleviated or entirely discontinued, the clot expands slightly, but sufficiently so to push outward on the ID of the catheter, resulting in a risk that a catheter utilizing this approach will remain plugged and consequently rendered unable to effectively aspirate the clot if vacuum is restored.

By focusing upon static suction operating at or near full vacuum, for example, about −29.2 in Hg, without helpful or effective indication of tip activity, the prior art has heretofore been limited in lacking continuous feedback of conditions of the aspiration catheter. Although cyclic aspiration patterns have, to date, been suggested, the effectiveness and practice thereof has been severely limited.

Furthermore, because conventional aspiration systems generally still utilize static vacuum pumps, they have yet to enable reliably effective treatments for acute ischemic stroke, nor are they capable of universally interfacing with known and later developed aspiration catheters.

In this regard, some conventional aspiration systems employ dedicated catheter tubing sets sold and packaged separately. An additional drawback resides in the fact that the prior art clot extraction approaches are not compatible with neurovascular revascularization stent retrievers.

It would therefore be desirable to provide acute ischemic event therapies and optional wider functional applications which address and overcome these and other drawbacks of prior art approaches.

SUMMARY OF THE INVENTION

In accordance with these and other objects of the invention, there is provided a thrombotic extraction system which provides the advantageous option of applying cyclic aspiration effective for fatiguing a clot occluding a vessel.

In particular, the invention relates to a system directed to recyclable pumps able to interface with known and later developed catheters, making them universally smart catheter systems, with touchscreen, WiFi, and/or Bluetooth controls for thrombus aspiration and treatment.

Briefly stated, energy sources with touchscreen enabled control of changes in cyclic forces drive AI-based algorithms guided by human medical intervention to support universal aspiration catheter interfacing for acute stroke therapy.

There is disclosed, inter alia, processes and methodologies regarding use of a recyclable pump constructed of sustainable materials for the purpose of aspirating thrombi, among other bodies, within blood vessels, particularly advantageously, those vessels within the human brain, and those associated with PV and/or STEMI, etc.

According to embodiments, universally interfaced cyclic algorithms drive use of any known or developed aspiration catheters to treat acute ischemic stroke by providing a novel enhanced energy source.

An aspiration system according to the invention comprises a pressure controllable pump system (conveniently in a form of an integrated pump device), including a peristaltic pump driven by a stepper motor. A sensor is advantageously included and is used to measure the fluid pressure in the catheter. This value serves to provide feedback to control logic which decides if the pump should generate positive or negative pressure to extract the clot. A combination of positive and negative pressures effectively forces the clot to reliably degrade and pass through the catheter.

In the case that the clot happens to plug the catheter, the algorithm instructs the pump to switch to a purely negative pressure mode (uniform vacuum) for a given time. If the pressure sensor indicates that the plugged or corked condition has changed, then the logic reverts back to a cyclical pressure mode for extracting the clot, sending corresponding instructions to the peristaltic pump.

If the measured pressure remains below a specified value, the system assumes that the clot has fully corked the catheter, and a message screen directs the user to remove the catheter while the pump is in constant aspiration mode (negative pressure) for example, full vacuum as employed in conventional systems.

A pressure sensor provided according to embodiment of the invention constantly monitors the pressure in the catheter and controls the pump accordingly in accordance with a selected algorithm suited to the aspiration catheter being used and which is advantageously implemented by processor control to stay above a lower pressure limit (Plower) and below an upper limit (Pupper).

In a particularly advantageous mode of operation, in which cycles of alternating pressure are applied, the clot is pulled towards or into the catheter under higher vacuum and released under lowered vacuum. This cycle advantageously repeats several times per second. The cyclic strain on the clot causes it to break under the applied repetitive alternating stress. When a broken-off portion of the clot is smaller than the ID of the catheter, the catheter is operated so as to aspirate the clot under free-flow conditions. In accordance with an embodiment of the invention, if the vessel is still occluded, the catheter is advanced to the face of the clot again which causes the pressure in the catheter to be reduced indicating at least partial occlusion thereof, and the cyclic aspiration cycle is resumed.

In accordance with a particularly advantageous embodiment, when the device is activated, the pump aspirates blood out of the catheter and the pressure is monitored. If the pressure reaches the lower limit of the "smart range," the pump reverses and infuses blood into the catheter to raise the pressure. When the rising pressure reaches the upper limit of the "smart range," the pump reverses and aspirates again.

For purposes herein, the term "Smart Range" refers to a selected and controlled lower and upper range of vacuum values (the terms "PLower" and "PUpper," respectively). Similarly, the term "Smart Mode" identifies an option setting which serves to cyclically approach the lower and upper range without exceeding either, controlled by a selected algorithm suited to a particular catheter being used.

It has been found that higher frequencies break up a clot faster and more effectively than other approaches. The frequency of the cycling is dependent on how fast the pump can change the pressure. Parameters controlling frequency relate to software, hardware and system considerations.

For example, software parameters that affect frequency include predetermined selected upper and lower pressure limits (PUpper and PLower), speed and acceleration rates of the peristaltic pump rotor and sampling frequency of the pressure sensor.

Hardware parameters that come into play include compliance of tubing from sensor to catheter (stiffness and length), compliance of tubing from sensor to pump (stiffness and length), stiffness of pump tubing and volume per revolution of the pump rotor (tube ID and rotor diameter).

System parameters which also serve to determine cycle frequency include compliance of the catheter being used, compliance and characteristics of the particular clot being aspirated and amount of any air being present between the clot and the pump rotor.

The parameter thought to have a particular impact on cyclic frequency, and thus performance of the inventive approach, is the amount of air in the system. Consequently, it is highly preferable that the system be fully primed before use and stay primed during subsequent operation. For example, a loose RHV (Rotating Hemostasis Valve) may allow air to enter the system under vacuum and adversely impact the effectiveness of the applied cyclic determining algorithm.

In accordance with a particularly advantageous embodiment, the pump can self-prime at the start of a procedure. According to this approach, once the user tracks the aspiration catheter, bring the tip near the location of the clot, the pump can be connected and primed. The connection between pump and catheter (or catheter RHV) can potentially introduce an air bubble into the tubing. But the distance from the bubble to the pump rotor is fixed and therefore the volume is known. The pump can be operated to aspirate this fixed volume (ideally including an added safety factor) to prime itself.

A thusly primed pump will operate at a relatively high cycling frequency. Any air introduced into the system will reduce substantially such frequency. The system can optionally and advantageously monitor the cycling frequency, and provide feedback to the user at any time reduced frequency is detected, indicating the likelihood that the system needs to again be primed.

The control system determining the performance state of the pump optionally instructs the pump to operate as a purely static aspiration device, or as a smart device that uses the pressure sensor to determine how to best remove a clot.

In accordance with this optional embodiment, there are two operational modes. These include employment of an Adaptive Pulsative Algorithm (APA Mode) and a Static Mode in which pump aspirates at uniformly maintained vacuum with no feedback from the provided pressure sensor.

Since the system optionally uses a positive displacement pump, such as for example a peristaltic type pump, the amount of blood pumped is proportional to the rotation(s) of the pump rotor and pressure. The pump can calculate and monitor the volume of blood pumped throughout the thrombotic extraction procedure. This volume can optionally be displayed to the user.

The blood volume can be compared to a settable limit by the processor which can optionally stop or slow the pump if this limit is reached. The user can then be alerted of this condition and may be presented with options for proceeding.

According to a particularly advantageous feature of the invention, the system can detect a plugged catheter by monitoring the pressure as the pump aspirates. If the pressure remains above the lower limit PLower of the smart range, the pump is free-flowing and the user has not made enough contact with the clot to cause the catheter to experience reduced flow. If the pressure drops to the lower limit of the "smart range" and remains so, the catheter is determined as being plugged. The system can advantageously present this information to the user to give feedback on the presence of the clot.

In summary, it is believed that no one has heretofore combined positive and negative cycling pressure that can support longer and more flexible aspiration catheters with improved touchscreens to control the cycling patterns for all catheters on the market and being improved all of the time.

By providing an optimized (as opposed to maximized) vacuum pressure/aspiration flow rate/thrombus removal force, the pressure system for the first time places all under interactive operator control.

A clot aspiration pump system according to embodiment of the present invention advantageously operates as a vacuum/aspiration pump with a compact footprint, operable for allowing a physician to extract thrombus through their choice of an on label aspiration thrombectomy catheter or stent retriever catheters adapted to use of aspiration.

Additionally, a system according to embodiment of the invention is advantageously provided in a form which is environmentally friendly. As envisioned, the housing is optionally and advantageously sourced from recycled materials and additionally, a clean take-apart process can optionally liberate and separate individual components for specialty material recycling and refurbishing.

A particularly advantageous feature of a clot aspiration pump is the system's compatibility with third-party thrombectomy catheters and/or stent retrievers. The pump system is advantageously configured as a sterile, single-use, battery-powered unit, and being compatible with aspiration indicated catheters.

The unit advantageously comprises in combination three components in one integrated device, including the components of tubing, a collection canister (reservoir), and an aspiration pump. A pump system according to embodiment of the current invention is advantageously agnostic to a specific catheter, controlled by software developed based upon features of current commercially available aspiration catheters.

A user-friendly touch screen is advantageously provided, which allows for the operator/physician to be engaged with the status of the pump and choose to activate the pump in either in adaptive mode (APA) or continuous aspiration (STATIC) mode.

The APA mode allows a pressure sensor output to adjust the operation of the pump, whereas the continuous aspiration mode (STATIC) is consistent with the actions of single-mode commercially available static aspiration pumps.

In accordance with a particularly advantageous embodiment, a pump system is integrated into a single unit which comprises a sterile single-use pump, standard nylon tubing, a sealed/disposable collection canister, integrated software, and a touchscreen display. Also, optionally, a battery pack and audio capabilities implemented by functional elements including, for example at least one speaker and associated audio components.

The touchscreen advantageously displays relevant conditions, such as for example, the battery level, status, operational mode, duration/time, pressure reading, and a graphical display of pressure, and allows the operator to select the appropriate catheter ID/length from a drop-down menu.

An advantageous embodiment according to the invention is intended to operate in a continuous aspiration and an adaptive mode. The continuous aspiration mode (STATIC), and the adaptive mode (APA) allows pressure sensor output to adjust the operation of the pump, allowing non-continuous aspiration. In STATIC mode, the current device operates in a manner essentially equivalent to conventional static vacuum aspiration pumps.

A system-provided catheter inline pressure sensor provides the measured information to a system microprocessor, which in turn instructs the pump to vary the amount and type of aspiration according to predetermined parameters. This feature advantageously mitigates patient blood loss, and provides a facilitated means for disrupting the morphology of the thrombus, resulting in effective thrombus removal and a decrease in catheter blockage.

According to embodiments, there is disclosed a truly recyclable pump system for ischemic stroke treatment, programmable and adjustable via touchscreen interfaces.

While several embodiments of the present disclosure are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the an will recognize, or be able to ascertain using no more than routine experimentation, many equivalents to the specific embodiments of the disclosure described herein. It is, therefore, to be understood that the foregoing embodiments are presented by way of example only and that, Within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, Whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Reference throughout this specification to "one embodiment," "an embodiment," or similar language means that a particular feature, structure, or characteristic described in connection with the embodiment is included in at least one embodiment of the present invention.

Thus, appearances of the phrases "in one embodiment," "in an embodiment," and similar throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method.

Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method.

Additionally, the order in which a particular method occurs may or may not strictly adhere to the order of the corresponding steps or methodologies shown.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core 15, Intel Core I & Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e. g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e. g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Various preferred embodiments are described herein with references to the drawings in which merely illustrative views are offered for consideration, whereby:

Corresponding reference characters indicate corresponding components throughout the several views of the drawings. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

The above, and other objects, features and advantages of the present invention will become apparent from the following description read in conjunction with the accompanying drawings.

Features, aspects, and advantages are described below with reference to the drawings, which are intended to illustrate, but not to limit, the invention. In the drawings, like reference characters denote corresponding features consistently throughout similar embodiments.

Corresponding reference characters indicate corresponding components throughout the several views of the drawing. Skilled artisans will appreciate that elements in the figures are illustrated for simplicity and clarity, and have not necessarily been drawn to scale. For example, the dimensions of some of the elements in the figures may be exaggerated relative to other elements to help to improve understanding of various embodiments of the present invention.

Also, common but well-understood elements that are useful or necessary in a commercially feasible embodiment are often not depicted in order to facilitate a less obstructed view of these various embodiments of the present invention.

BRIEF DESCRIPTION OF THE DRAWINGS

FIGS. 7A and 7B combined are a simplified operational flow chart depicting a basic operation of a pump system according to an embodiment of the invention;

FIG. 17A is a side perspective view of a system according to an embodiment of the invention which includes an integral clot catcher;

FIG. 17B is a top perspective view of the embodiment of FIG. 17A; and

DETAILED DESCRIPTION OF THE PREFERRED EMBODIMENT

Figure 1A:
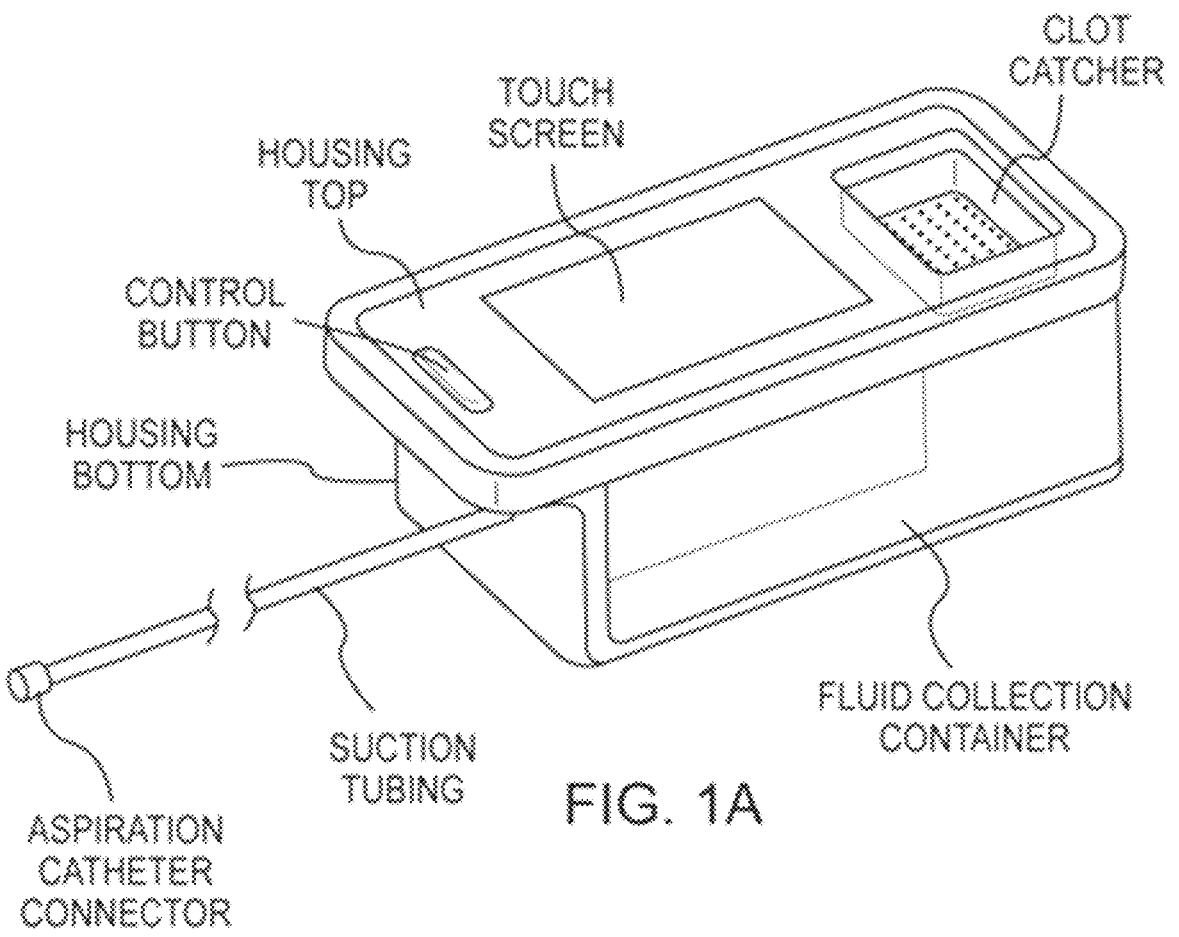
FIG. 1A is a CAD model perspective view depicting an example of a pump system in accordance with an embodiment of the invention.

Terms used herein as defined according to the intended definitions in the context of the present disclosure are now set forth herein.

Advantageously, there are two modes of operation. The SMART Mode which uses the Adaptive Pulsative Algorithm when in the APA Mode, and STATIC Mode in which the pump aspirates at essentially constant vacuum with no feedback from the pressure sensor.

The term "SMART Mode" is used herein to refer to the mode in which the pump system operates as a "smart device" controlled by an Adaptive Pulsative Algorithm ("APA mode") unique to a selected aspiration catheter, and constant aspiration in which the control system operates the aspiration as a purely static aspiration device ("STATIC Mode").

The terms "PUpper" and "PLower" refer respectively to defined upper and lower pressure limits used during APA mode.

Regarding use of the term "infusion," it will be understood that while often used in medical terms to describe an introduction of fluids, for example drugs, into the bloodstream, as used herein the term refers specifically to a reversal of aspiration resulting in an increase of catheter pressure.

Before referring to the drawings, a discussion of the various advantages of embodiments of the invention are presented.

Because of the approach of the invention, a direct connection of the catheter to the pump results in making possible shorter tubing lengths compared with convention aspiration pump systems. Additionally, for example, some systems employ catheter tubing sets sold and packaged separately. In accordance with embodiment of the present invention, the pump system can be supplied with its own connected, sterile tubing.

Embodiment of the present invention optionally provides audiovisual feedback during a thrombotic extraction procedure (i.e. w/video screen). Audio and visually displayed information within the physician's reach and line of sight advantageously allows rapid response by the physician/operator in selecting operational changes as needed. A speaker can optionally verbally indicate to the operator conditions at the tip of the catheter, and can also gives prompts.

Automatic shutoff according to an embodiment of the invention when a clot is cleared and also in "Free Flow" results in less patient blood loss. The blood displacement in Free Flow is significantly less than in conventional aspiration systems.

Embodiments of the present invention are capable of producing pressure cycles for effective removal of different types of clot using different catheter inner diameters. Positive and negative (vacuum) pressure cycle frequencies are adjustable for improved clot absorption/extraction (APA mode). Adjustable to catheter sizes and styles, proprietary algorithms for APA/cyclical suction for all catheters are possible.

Accelerated clot removal setting can increase the intensity of the frequencies when tougher clots are encountered.

Embodiments of algorithms of the invention customizable to be formulated for soft clots, organized clots, atherosclerotic clots, and dense/fibrous clots.

An embodiment according to the invention is optionally compatible with neurovascular revascularization Stent Retrievers (in SR mode).

Embodiments according to the invention are capable of producing a vacuum pressure of at least Full Vacuum. (eg., −29.7 mmHg), and capable of being set to a "steady (static) vacuum" mode (in addition to the cyclic (APA) modalities) In accordance with an optional embodiment, the pump system is at least partially recyclable.

According to an advantageous has a built-in clot catcher in the canister. Optionally integrated into the actual pump or included inside the tubing.

Figure 1B:
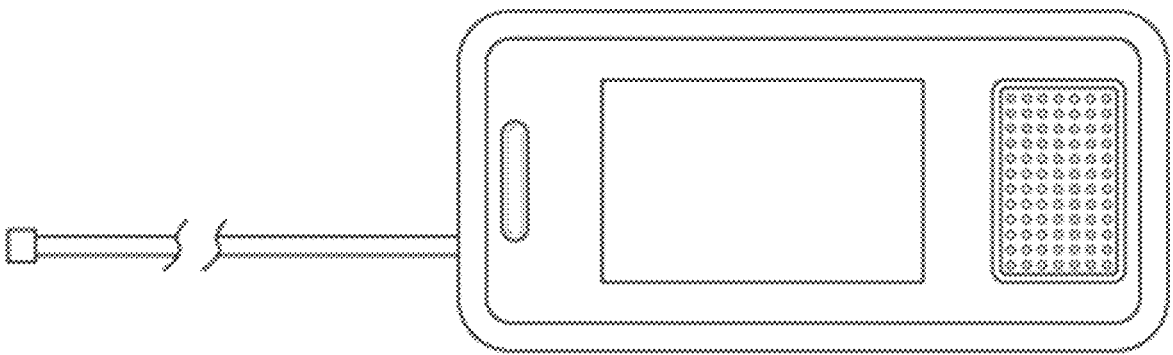
FIG. 1B is a top plan view of the pump system embodiment of FIG. 1A.

Turning now to FIGS. 1A and 1B, a CAD model of an example of a pump system according to the invention is shown in perspective view (FIG. 1A) and a top plan view (FIG. 1B).

As depicted, the exterior of the example of the pump device in FIGS. 1A and 1B comprises a suction tubing carrying a standard luer connector for hermetic mating with a conventionally available aspiration catheter, a housing, a touchscreen, a control button, a collection container, and a clot catcher for trapping a removed clot for examination.

The internal components with be described in greated detail with reference to further figures.

Figure 2:
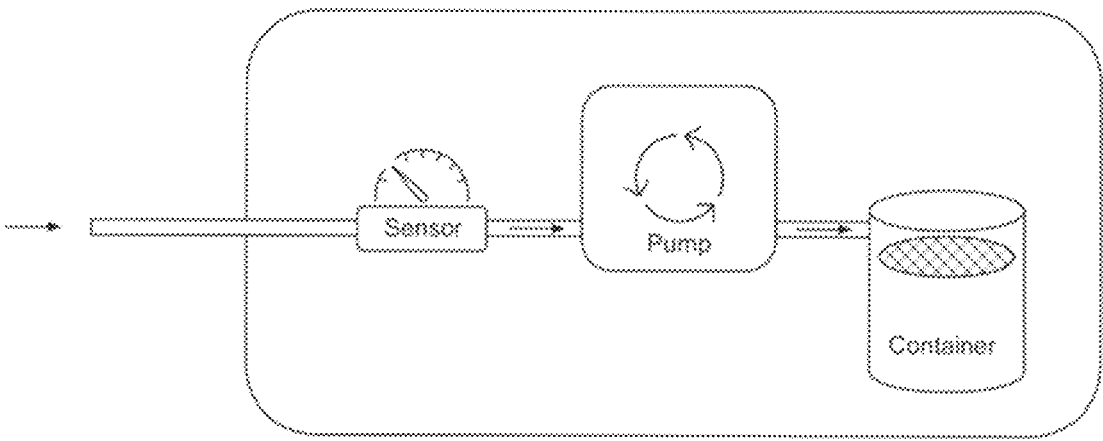
FIG. 2 depicts a schematic representation of core components of a system according to an embodiment of the present invention.

Referring to FIG. 2, a schematic representation of a core of a pump system according to the invention is shown, and which allows optional flexibility of a "Smart Pump" using selected algorithms designed for given aspiration catheters. As shown, a sensor is provided inline with the inlet tubing leading to a pump, advantageously provided by example as a peristaltic pump of a peristaltic pump driven by a stepper motor which includes an outlet connected with a container for collecting a removed clot or portions thereof. The sensor is used to measure the fluid pressure in the catheter, and this value is used by provided control logic to decide if the pump should generate positive or negative pressure to extract the clot, as will be described in greater detail.

According to a particularly advantageous embodiment, the stepper motor operates with micro stepping set at 32. The stepper motor takes 200 steps/revolution (360°/1.8°) when setup as full steps. With a setting of 32 microsteps/step the motor can perform 200 steps×32 microsteps/step, or a total of 6400 steps/revolution. Commands to the stepper motor advantageously occur every 20 ms.

As mentioned, the algorithm that controls the stepper motor uses the pressure sensor as the feedback device. Within the algorithm there are a set of parameters that define the upper and lower pressure limits and the speeds for clockwise (CW) and counterclockwise (CCW) rotation of the stepper motor.

An example of a suitable stepper motor is a standard NEMA17 stepper motor. The motor uses, for example, a DRV8825 stepper motor driver-based circuit that requires commands to be in the form of numbers of steps and direction (CW or CCW). In the example, the provided circuit board sets the microsteps to 32, making one revolution equal to 6400 microsteps.

The algorithm in its most basic form defaults to ASPIRATION mode. In this regard, when the control button is pressed, the algorithm sends a command to perform a large amount of steps (in this case, microsteps) at a constant rotational speed (microsteps/sec).

If the pressure sensor output is greater than the PLower pressure limit, the algorithm will continue commanding the motor to keep moving at the same rotational speed.

The algorithm runs on various loops. One of them will continue to send a new command to move the same amount of steps and at the same speed as long as the pressure sensor output indicates the system is in a FREE FLOW state (no interaction with the clot).

If a pressure drop occurs due to a clot covering the catheter tip and the pressure sensor output is below the PLower limit, the algorithm will command the motor to immediately change the direction of the motor. This starts an increase in pressure within the catheter to push the clot enough to loosen it from within the catheter.

This process repeats itself until the clot is aspirated fully and the pressure sensor output returns to the Free Flow pressure value or the occlusion cannot be resolved.

The algorithm operates by setting operational states, with the main states being ASPIRATE, INFUSE and STATIC PLUG.

ASPIRATE and INFUSE are the most demanding and require a fast response both from the sensor and the stepper motor/pump. In order to make sure that the response is not slowed down by unnecessary command checks, the main loop consistently checks at 20 ms intervals the position and velocity of the stepper motor. Each command sent to the pump takes longer than 20 ms to complete. Therefore, advantageously, every time an interrupt is triggered within the microprocessor, the status of the pump and the pressure sensor are checked and a new command is sent with updated values.

This guarantees that the pump will not remain idle at any point during the switch between ASPIRATE and INFUSE states. In addition, the system can quickly respond to changes in pressure due to changes in the interaction between the clot and the catheter.

At the beginning of the extraction process, the user presses the control button to start. The algorithm starts with aspiration at a constant rate.

If at any given time the tip of the catheter is in contact with the clot, the pressure sensor reading will drop. There are two events that create this pressure drop.

If the clot does not fully cover the catheter opening, the pressure will drop to some level. If this level is above the pressure lower limit (PLower) the pump will continue to aspirate at a consistent rate.

If the clot fully covers the catheter, the pressure will continue to drop. One of the following cases will apply.

If the clot is fully aspirated due to the increased suction, the pressure level will return to initial levels and the pump will remain in aspiration mode until the user stops the pump to terminate the process.

If the clot remains fully covering the catheter, the pressure level will drop until the PLower limit is reached. At this point, the algorithm commands the stepper motor to change direction and now increase the pressure.

At this point the pump is rotating CW in order to increase the pressure within the catheter in order to dislodge the clot slightly. Once the pressure reaches the PUpper limit, the algorithm instantly commands the stepper motor to aspirate. This process of changing stepper motor direction will repeat itself until one of two things occur.

The clot is fully aspirated. The stepper will remain in aspiration mode until stopped by user.

After a predetermined amount of time of increasing and decreasing pressure cycles the algorithm will switch to a static aspiration mode (STATIC mode). In this mode, the pressure drops to vacuum and allows (if possible) the clot to be aspirated. This mode also has a predetermined time limit. If the clot is not aspirated within this time, a screen is displayed indicating that the catheter needs to be removed. The pump will maintain the vacuum state until the user presses the control button.

As will be discussed further, a combination of positive and negative pressures force the clot to degrade and pass through the catheter. In the case that the clot plugs the catheter, an applied algorithm will switch to a purely negative static pressure mode for a given time. If the pressure sensor indicates that the plugged or corked condition has changed, then the logic reverts back to extracting the clot. If the pressure remains below a specified value, the logic of the system assumes that the clot has fully corked the catheter, and a message screen advantageously directs the user to remove the catheter while the pump is in constant aspiration mode (negative pressure).

Figure 3:
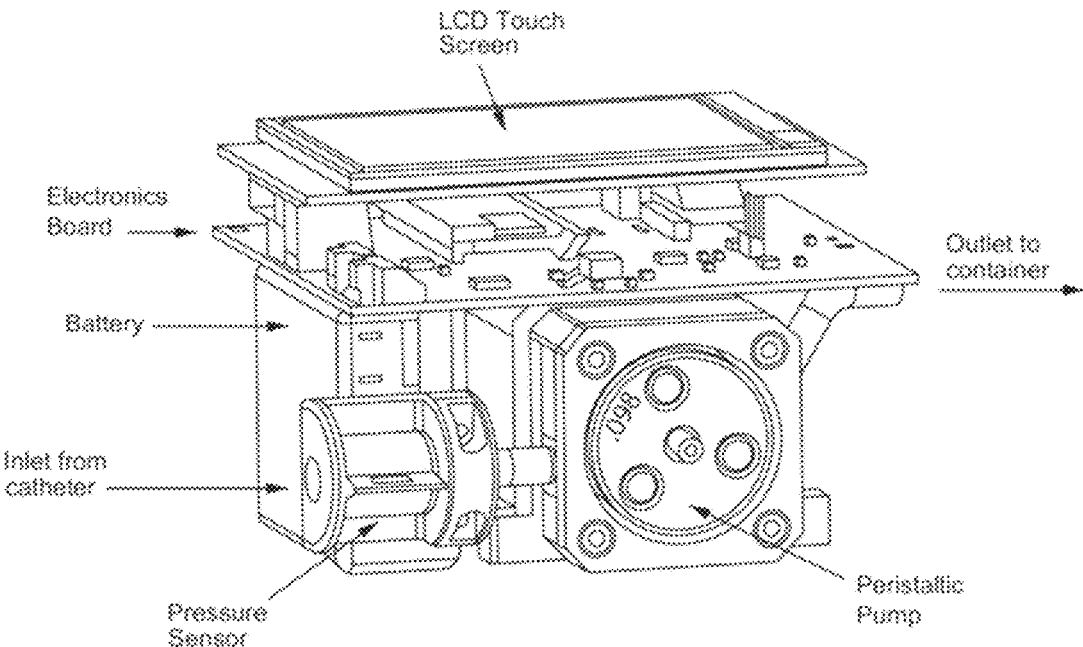
FIG. 3 is a perspective view of a CAD model depicting an example according to an embodiment of the invention.

FIG. 3 depicts a perspective view of a CAD model showing an example of an embodiment of an aspiration pump system according to an embodiment of the invention. As shown, the illustrated pump system includes pressure sensor, inlet from the catheter, a peristaltic pump, a battery power supply, an electronics board for microprocessor control of the pump, an LCD touch screen and an out let to a collection container.

Figure 4:
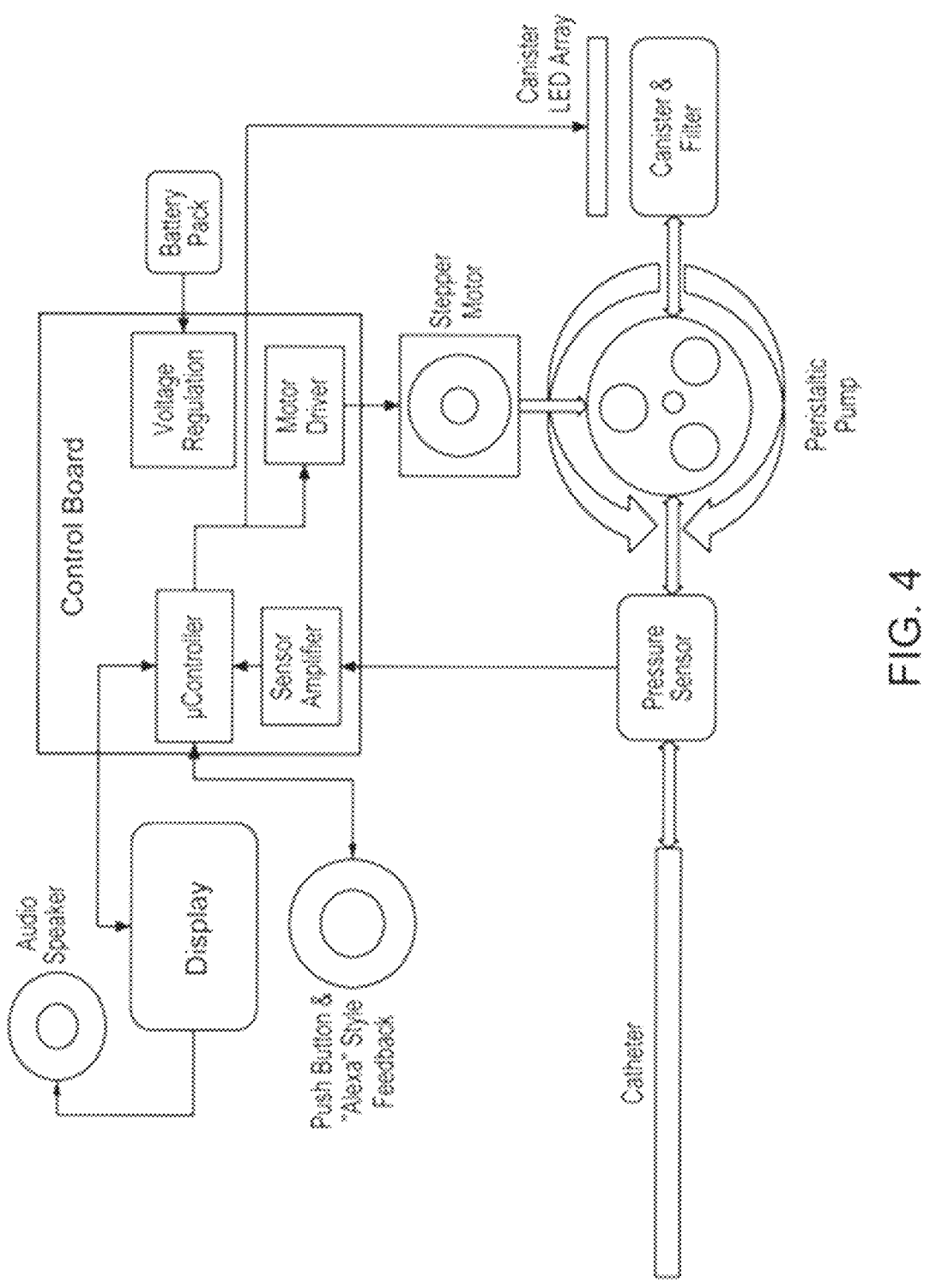
FIG. 4 is a schematic diagram which depicts an aspiration pump system according to an embodiment of the invention.

A schematic diagram detailing the elements of an advantageous embodiment of a pump system of the invention is depicted in FIG. 4. The depicted pump diagram shows the embodiment as comprising a display, a control board, a button and a battery pack. The control board advantageously includes a micro processor controller, a sensor amplifier, a voltage regulator and a motor drive.

A catheter leads to the pressure sensor which is connected with peristaltic pump driven by a stepper motor, and an outlet of which is connected to canister and clot collection filter.

Figure 5:
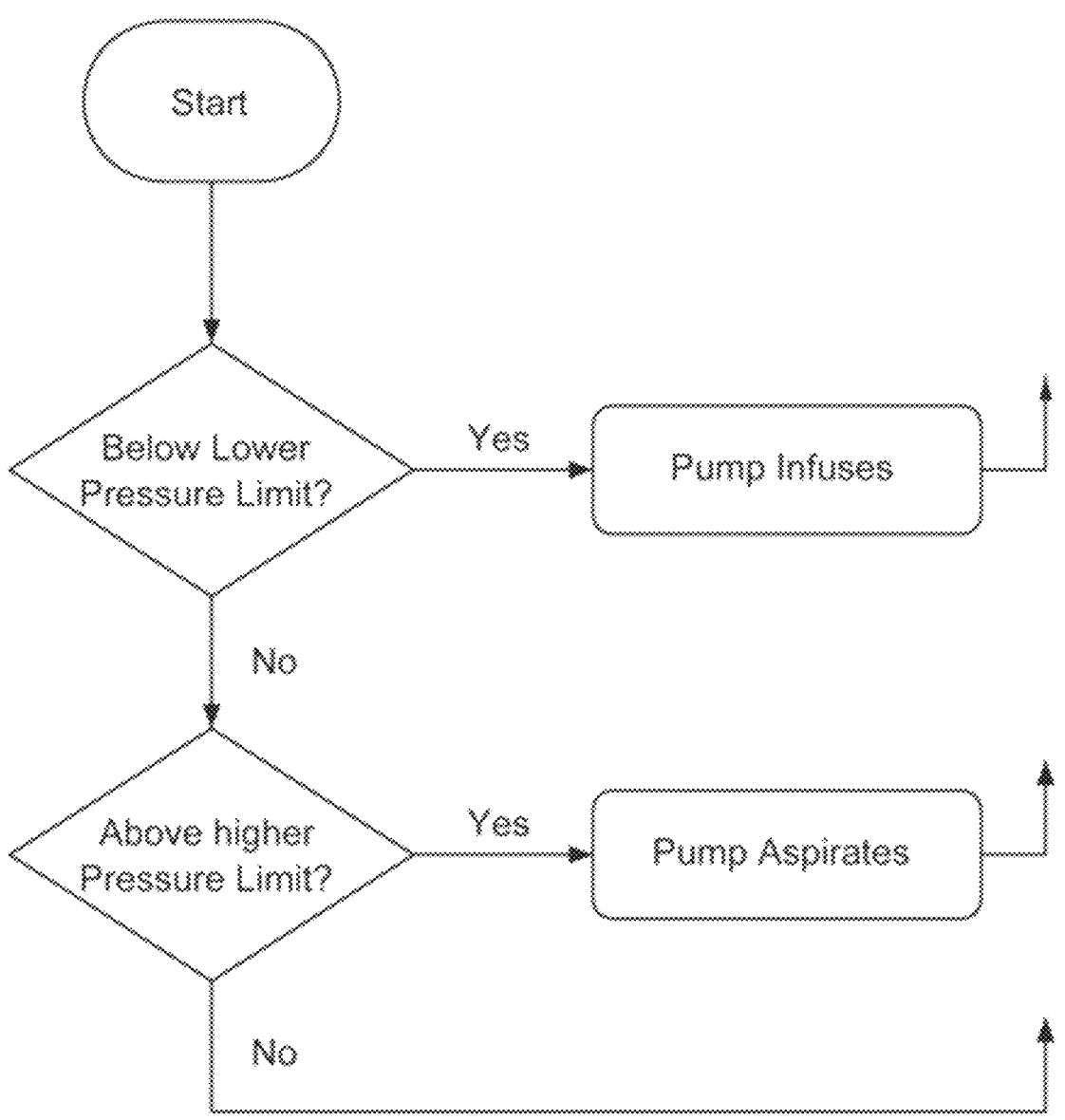
FIG. 5 is a simplified flow chart visually depicting how an APA mode algorithm according to an embodiment of the invention is implemented.

Referring to FIG. 5, a simplified flow chart visually depicting how an APA mode algorithm according to an embodiment of the invention is implemented. After the system is started, the sensor reports whether the pressure in the catheter is below a lower pressure limit (Plower). If yes, the pump is instructed to infuse.

Figure 6:
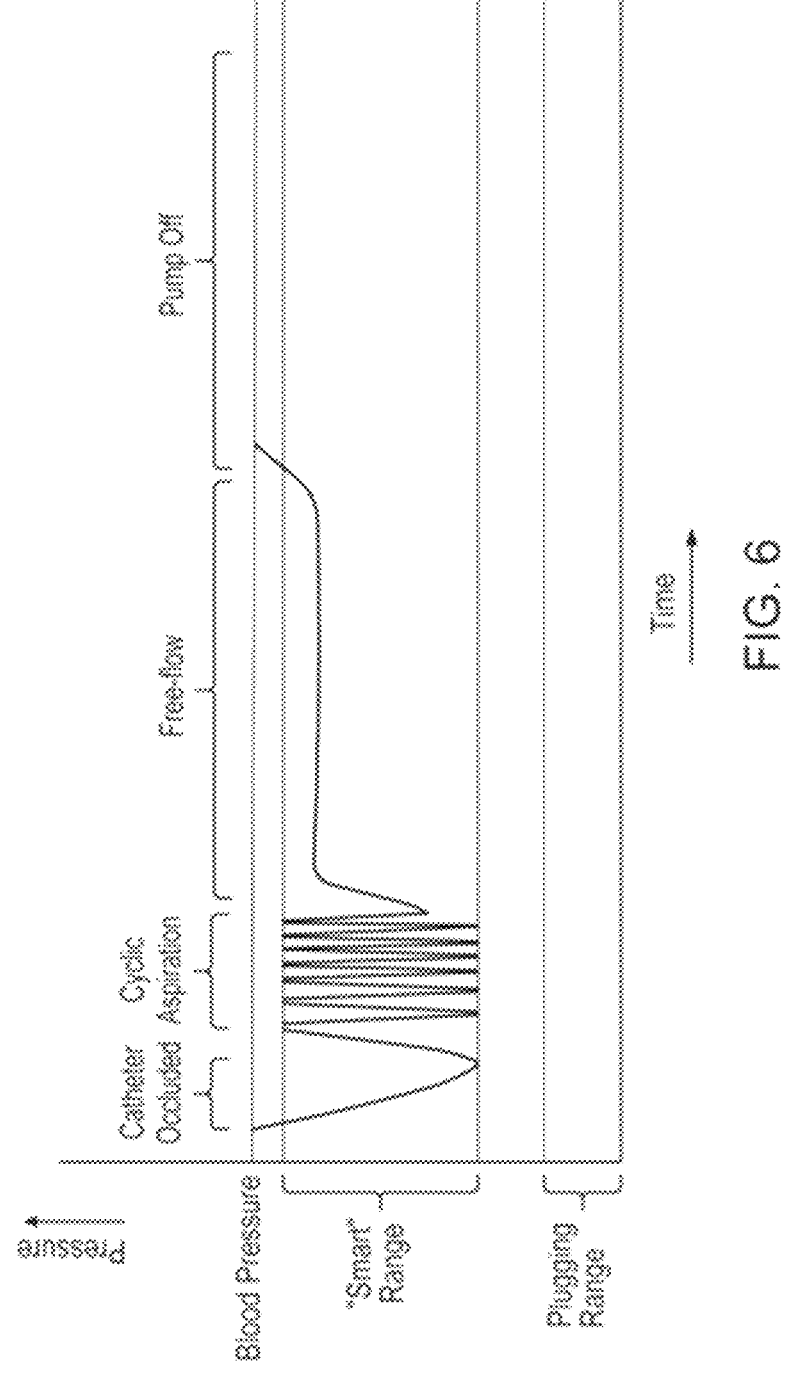
FIG. 6 is a graphical representation of cyclic aspiration performed over time when in APA mode according to an embodiment of the invention.

FIG. 6 graphically represents pressure variances over time when cyclic aspiration is performed in APA mode according to an embodiment of the invention. Cyclic aspiration is applied, maintaining oscillating pressure conditions varying between PLower and PUpper.

For purposes of disclosure, it is noted that there are five modes (flow states) in which the pump according to embodiment of the invention operates within. These include a READY mode, a FREE FLOW mode, an EXTRACT mode, a PLUG mode and a REMOVAL mode. Each is addressed below.

In READY mode, the pump has been primed and is ready to operate. The pump begins operation once the start/stop control button (see FIGS. 1A and 1B, and 4) is pressed.

When in FREE FLOW mode, the pump is in aspiration mode (negative pressure). The measured fluid pressure is below a defined upper value (Pupper) and above a lower defined value (PLower), and therefore no occlusion or partial occlusion is assumed.

When in EXTRACT mode when the pressure value drops below a defined value, it indicates that a partial or full occlusion of the catheter has occurred. The algorithm constantly generates positive and negative pressures based on the pressure levels measured. The amount of time that the pump is in the EXTRACT state is stored and compared to a defined limit. If this limit is exceeded the pump state switches to PLUG, indicating a blockage of the catheter.

Consequently a PLUG mode is initiated when the EXTRACT state exceeds a defined amount of time. The algorithm switches to a PLUG state, indicating that the pressure is lower than the defined level (PLower). The pump continues to create negative pressure for an additional amount of time. If the pressure increases above the defined Plower value, the pump returns to the EXTRACT state. If not, a message indicates that the catheter is corked, and it is recommended that the catheter be removed. The pump state switches to REMOVAL mode.

In REMOVAL mode, the pump maintains a constant negative pressure to allow the removal of the catheter with the clot attached or inside of it. Once the catheter is removed, the user must press the start/stop button to switch the pump back to READY.

Figure 7B:
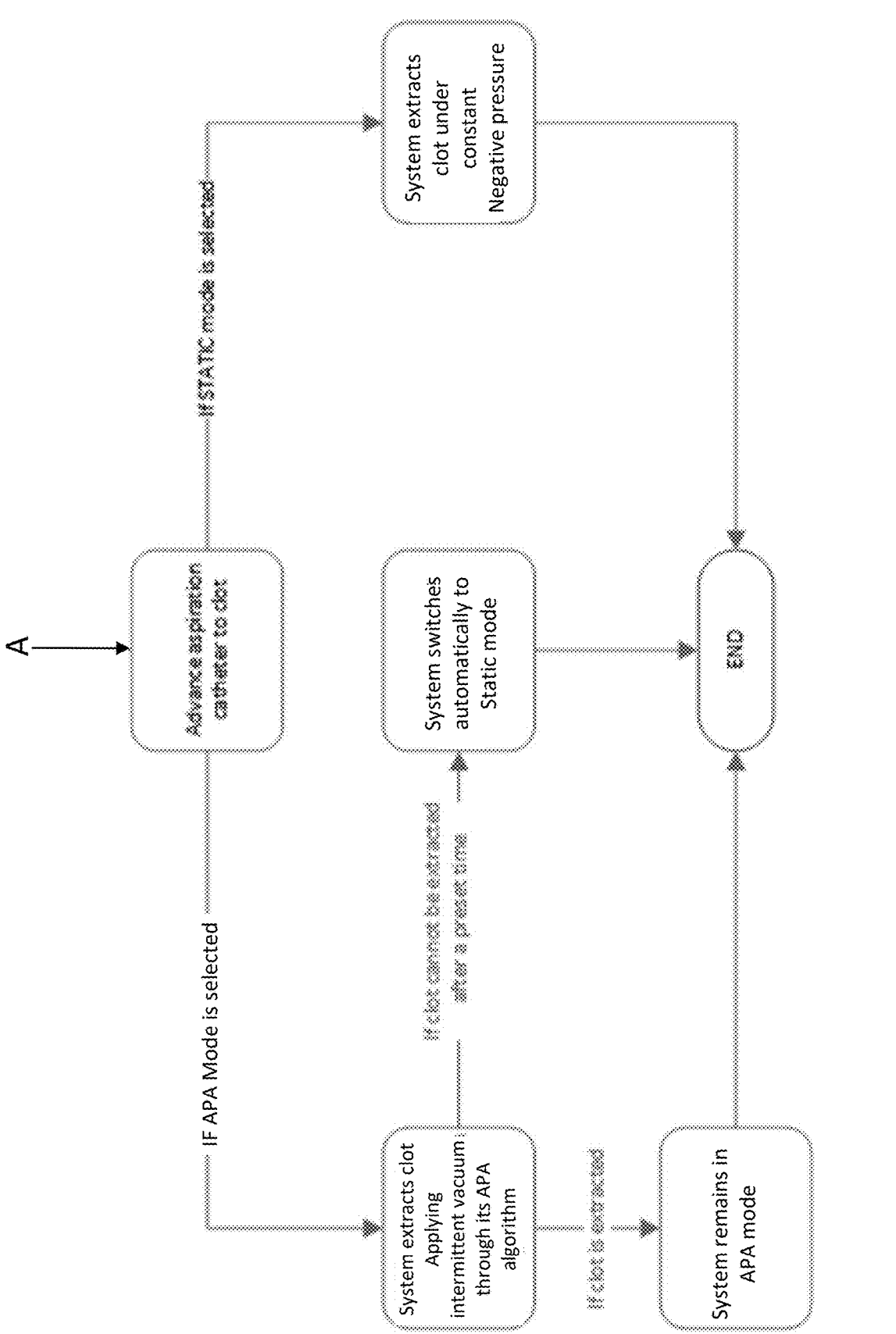
Figure 8A:
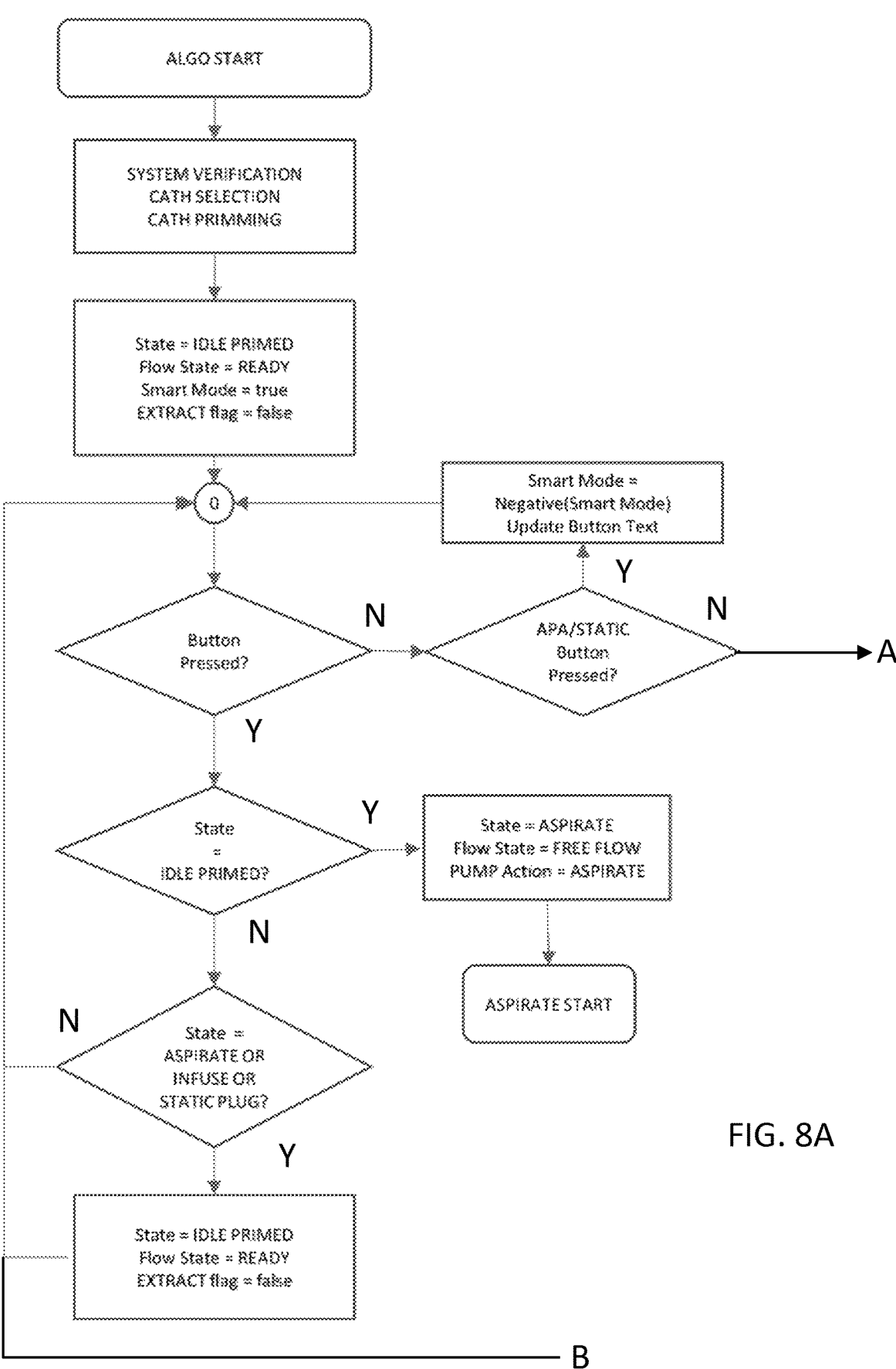
FIGS. 8A and 8B combined are a flow chart depicting the methodologies of the algorithm main loop according to an embodiment of the invention.
Figure 8B:
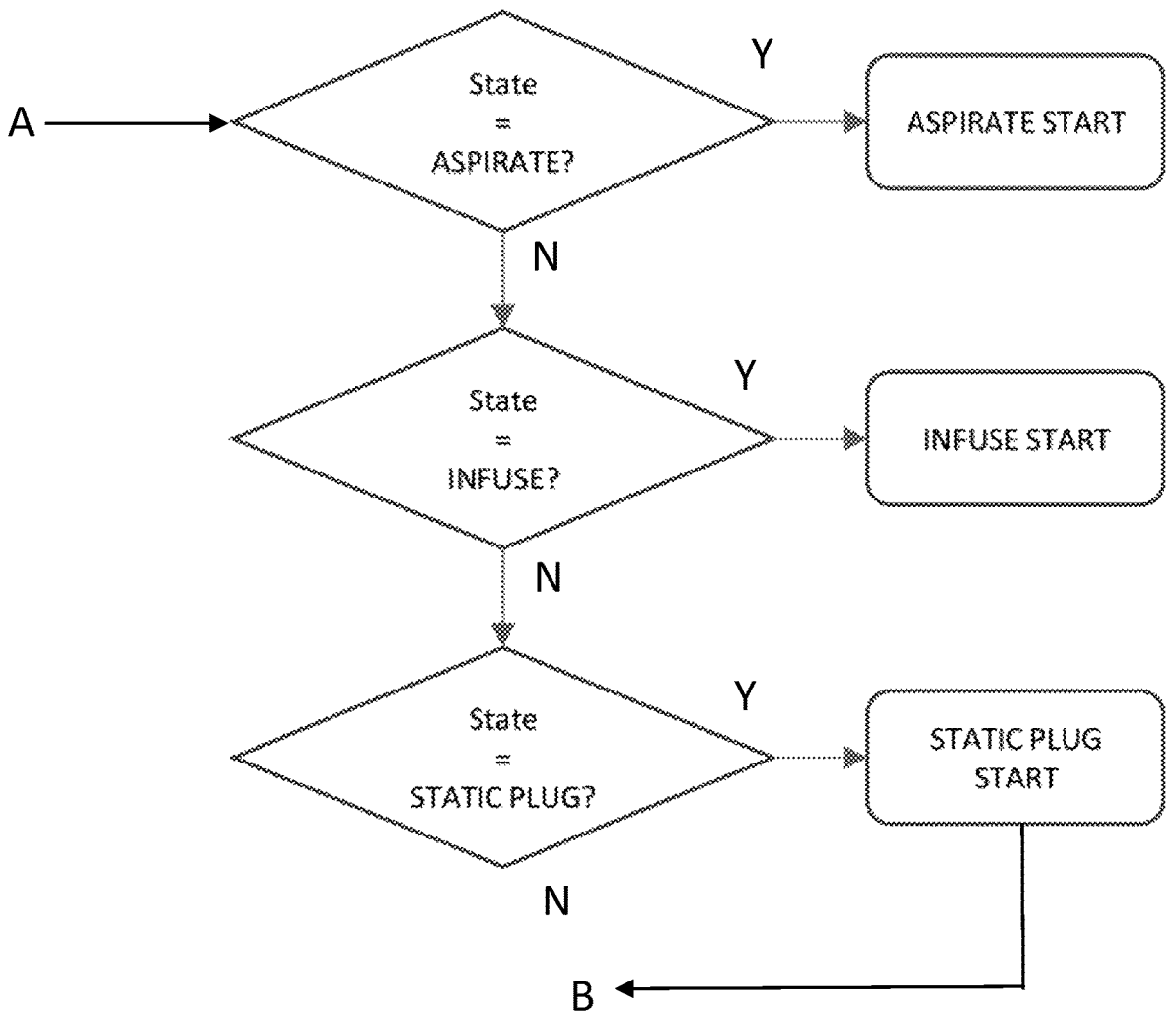
Figure 9A:
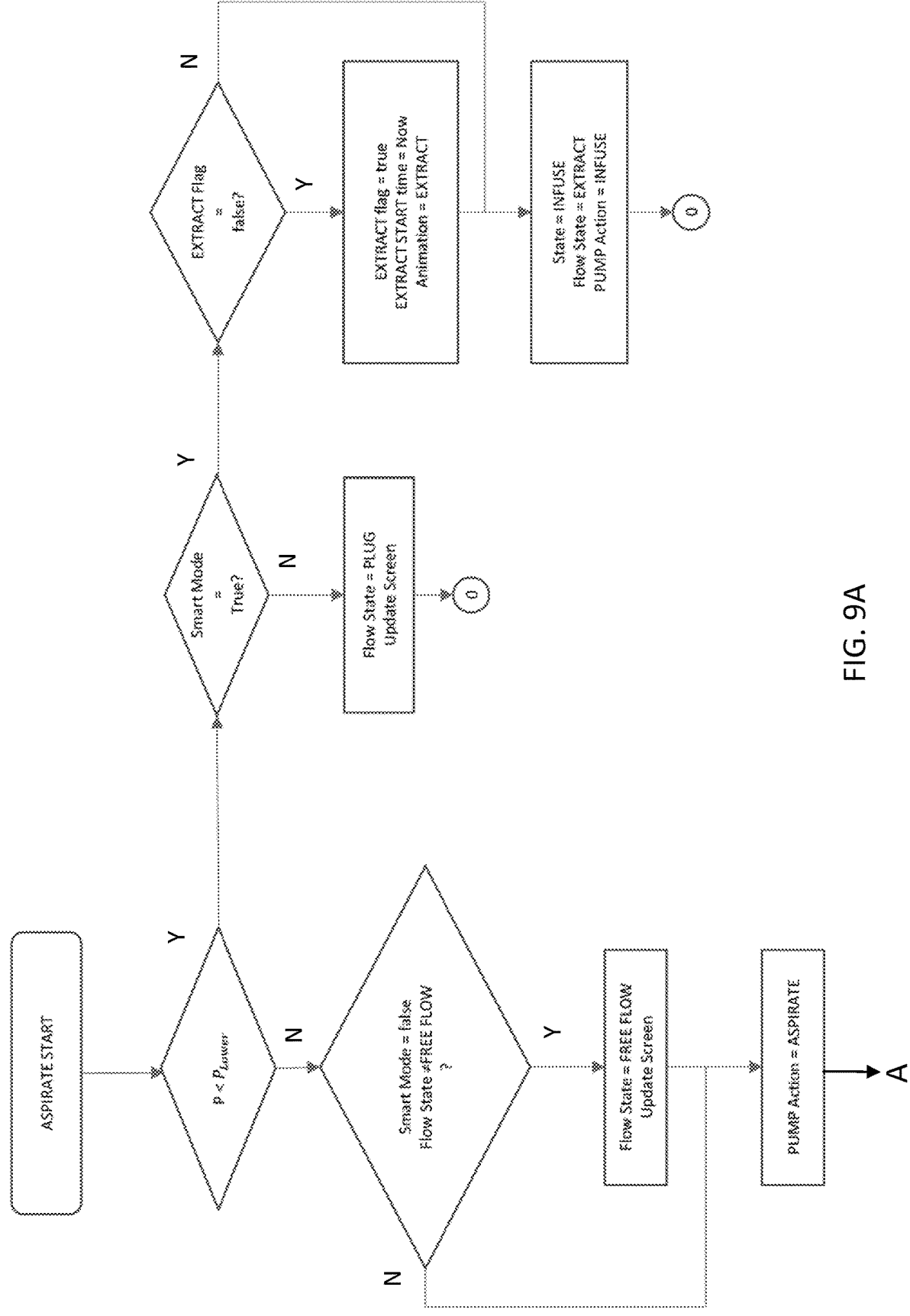
FIGS. 9A and 9B combined are a flow chart depicting an aspirate methodology loop of an algorithm according to an embodiment of the invention.
Figure 9B:
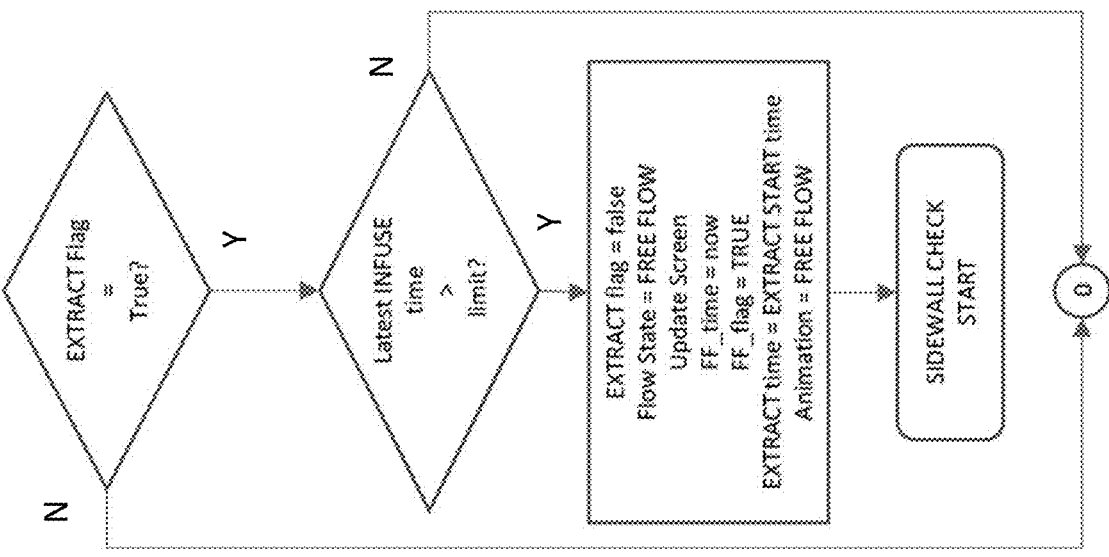
Figure 10A:
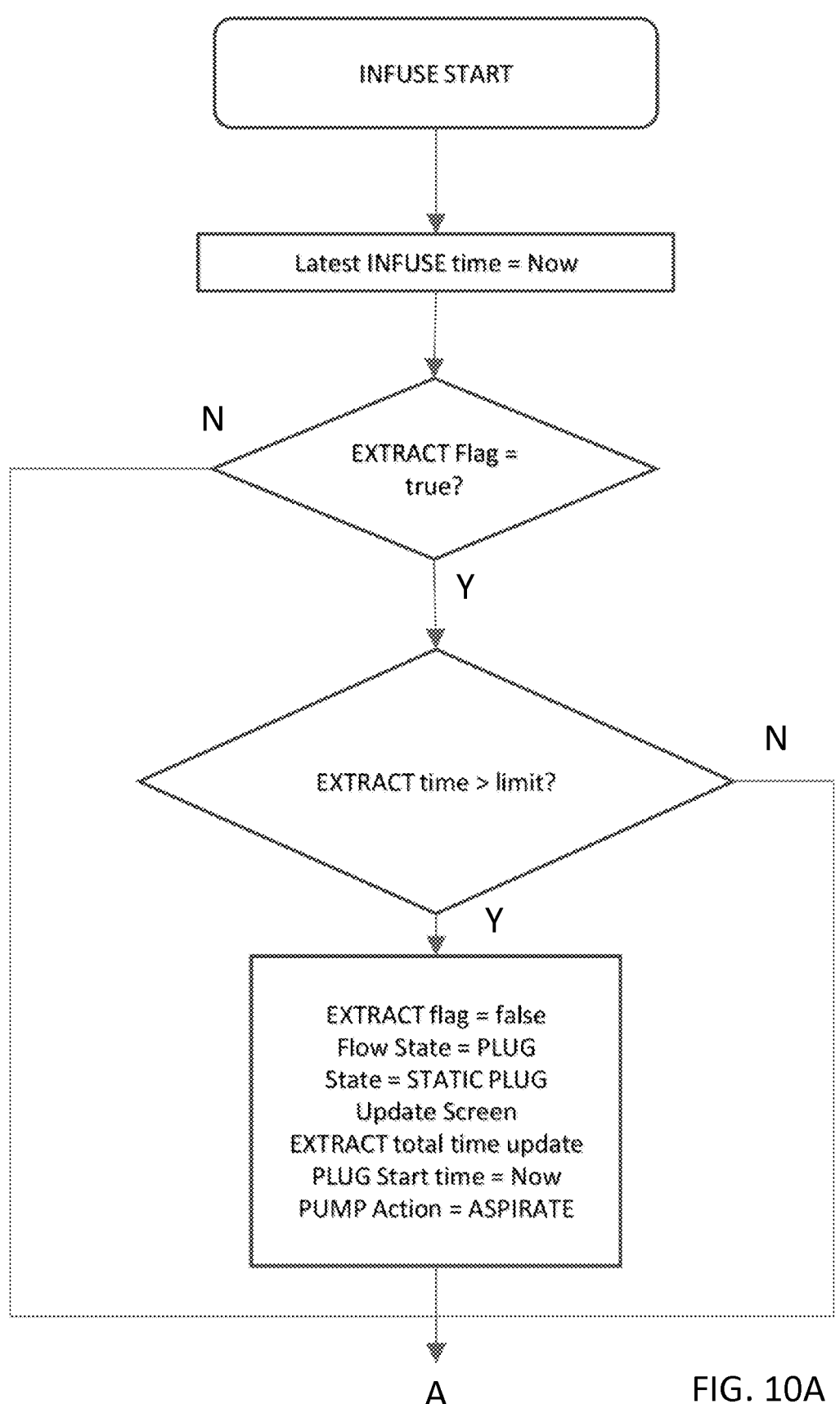
FIGS. 10A, 10B, and 10C combined are a flow chart depicting an infuse methodology loop of an algorithm according to an embodiment of the invention.
Figure 10B:
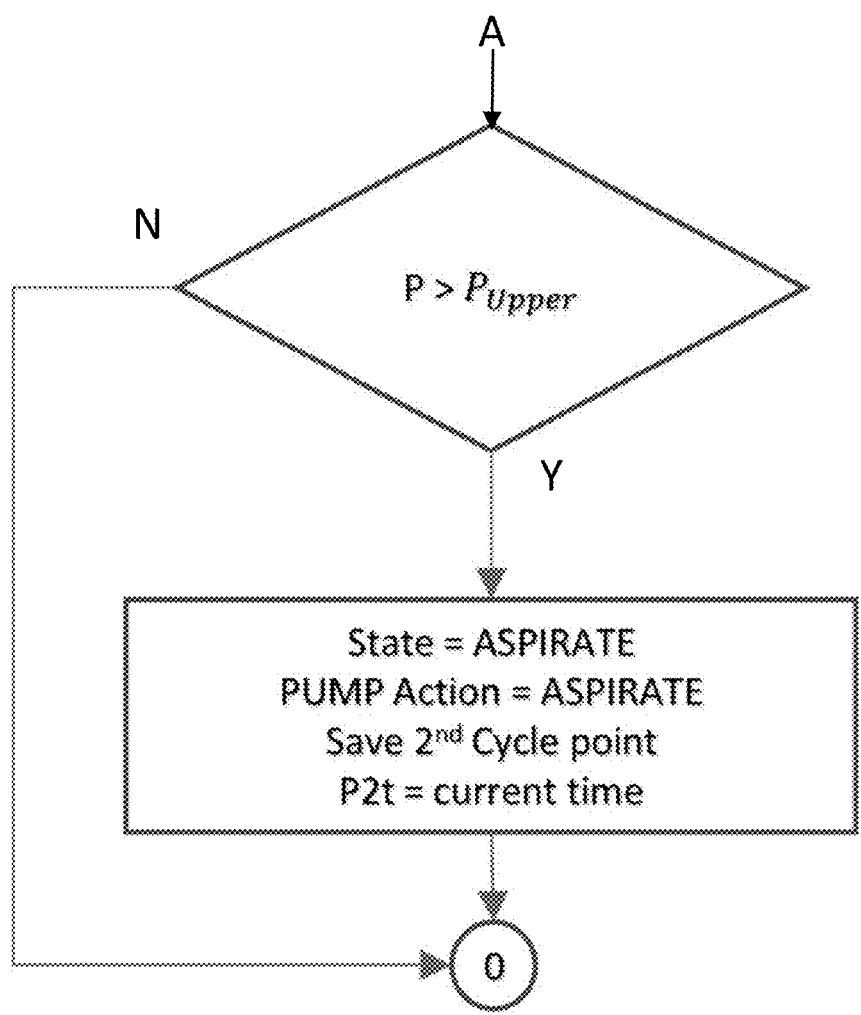
Figure 10C:
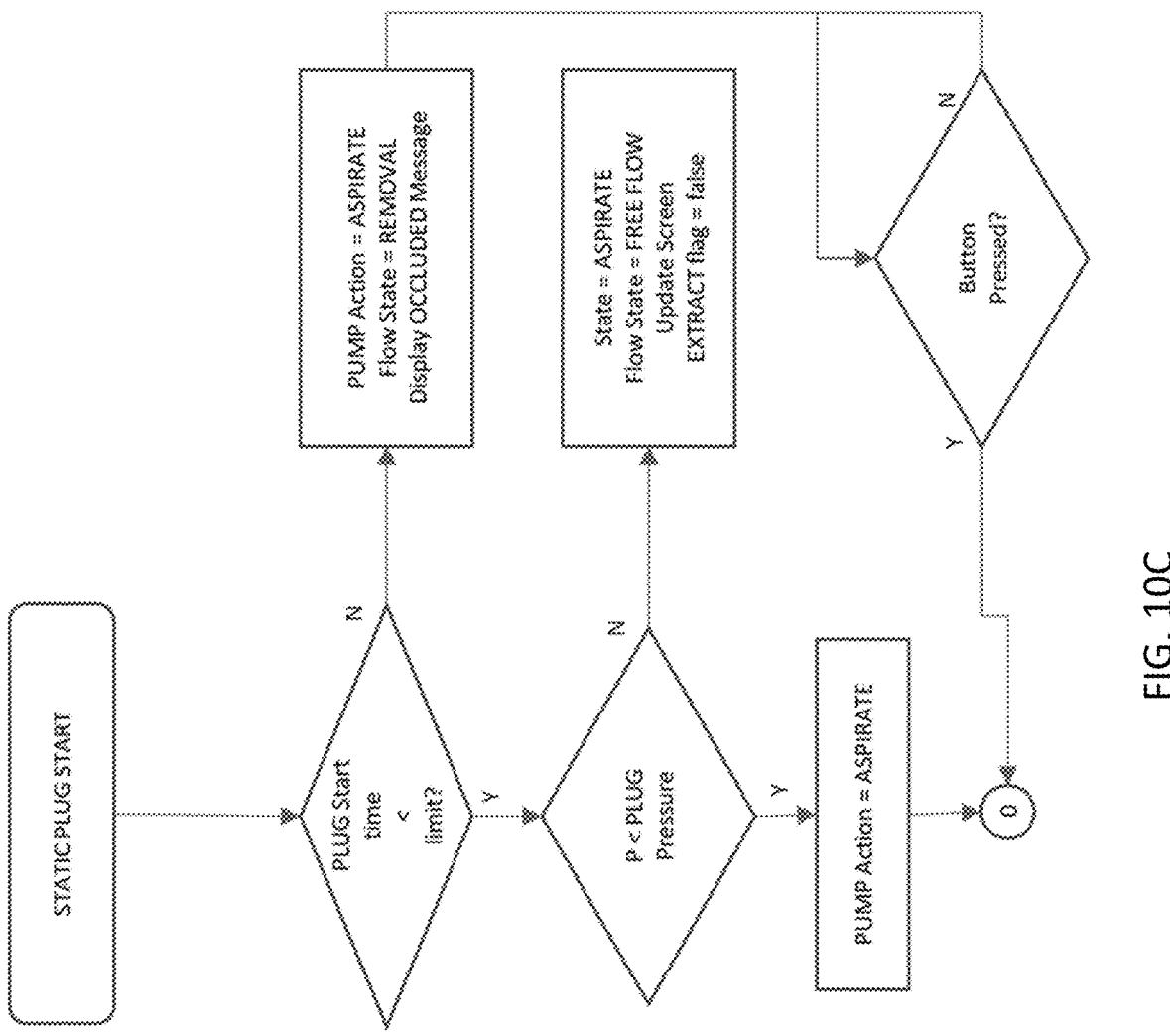
Figure 11:
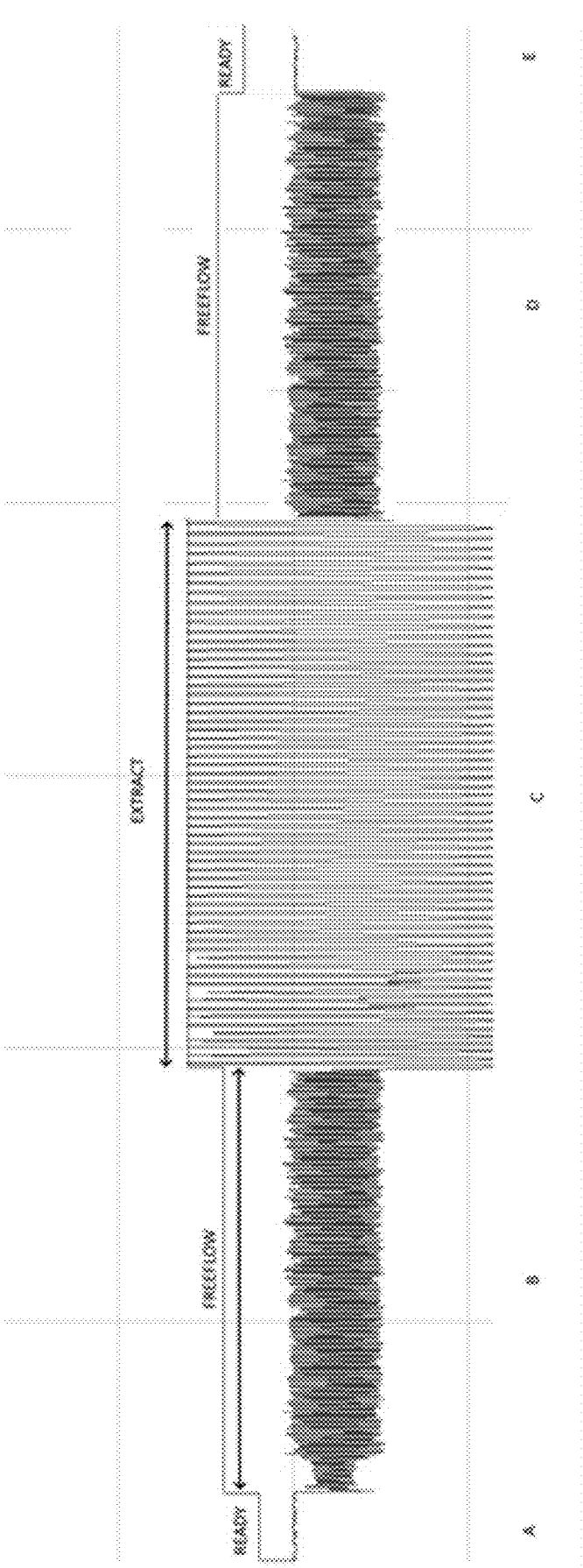
FIG. 11 is graphical representation of pump flow stages associated with a basis clot extraction process with minimal issues.
Figure 12:
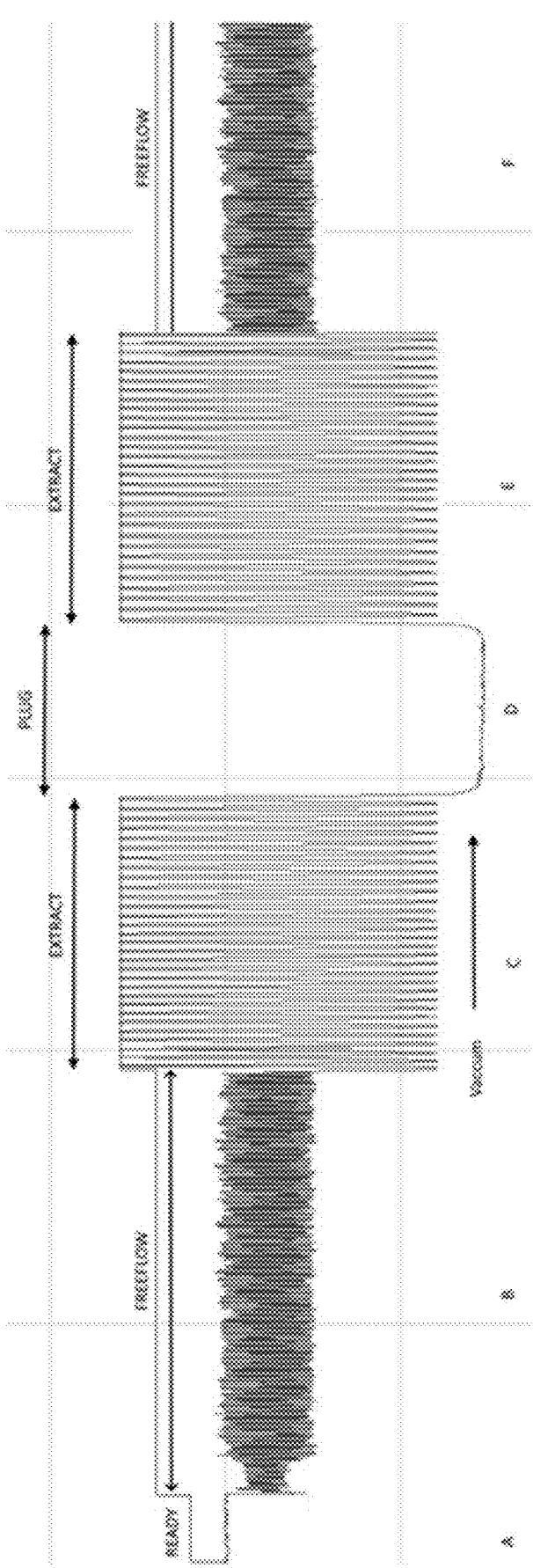
FIG. 12 is graphical representation of pump flow stages associated with a clot extraction process during partial occlusion.
Figure 13:
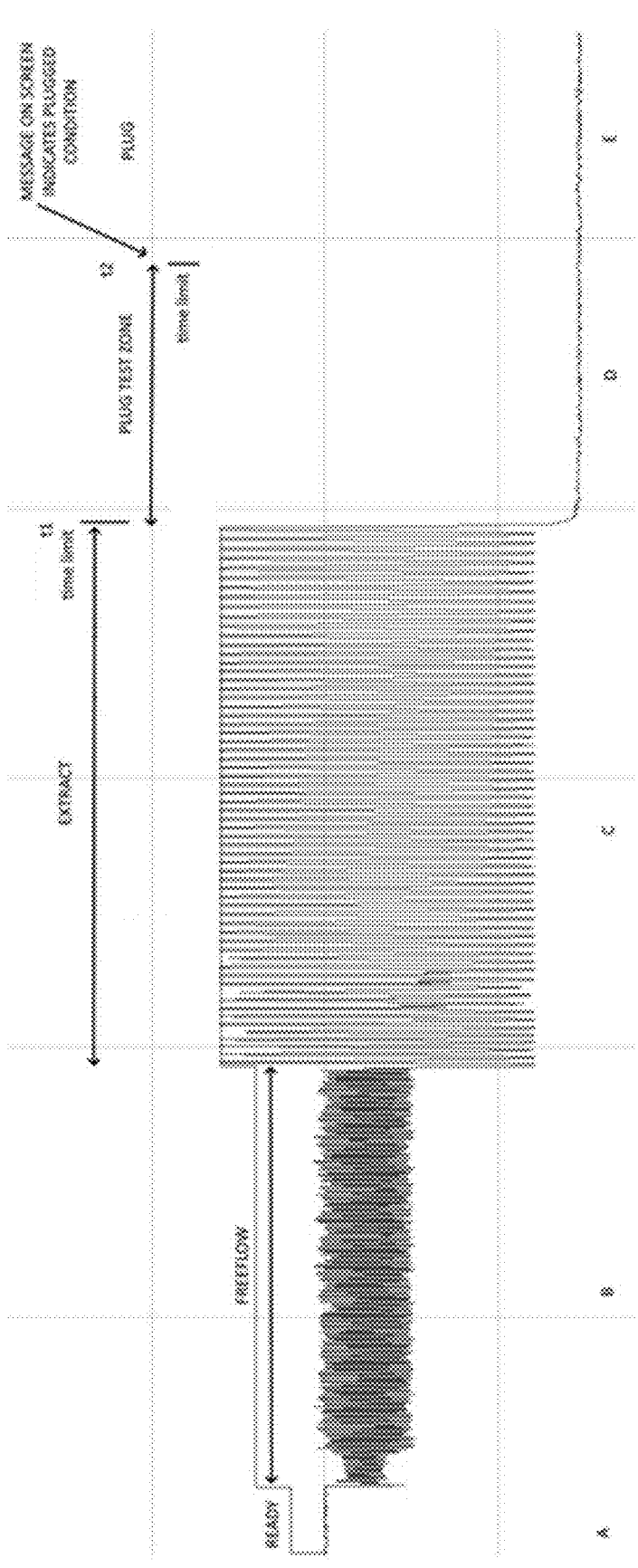
FIG. 13 is a graphical representation of pump flow stages associated with a clot extraction process terminating in a fully occluded catheter.

FIGS. 7A and 7B are a flow chart depicting process methodologies from START to END for both STATIC and APA modes.

Reference to "operational state" is used to describe the pump behavior along a main loop depending on the current flow state discussed above, as controlled by a selected pump algorithm.

Referring now to FIGS. 8A and 8B, a main loop is depicted in the illustrated flow chart. The flow chart begins in a start block and terminates in any of a start of ASPIRATE, INFUSE or STATIC PLUG. Each of these selections are depicted as flow charts in FIGS. 9A-10B.

Turning now to FIGS. 9A-9B, the depicted process begins with a start of ASPIRATE. The pump generates negative pressure creating a suction effect. If the pump is operating with the Smart Mode Off (STATIC mode) the aspiration will continue at a constant rate independent of the pressure sensor. If the Smart Mode is On (APA mode) the algorithm will determine how much to aspirate based on the pressure sensor value.

Referring to FIGS. 10A-10C, in INFUSE state, the pump generates a positive pressure on the fluid. This operational state only occurs during the EXTRACT state in APA mode. The algorithm will determine how much to INFUSE based on the pressure sensor value.

Also in FIGS. 10A-10C, a STATIC PLUG control state is shown. During the STATIC PLUG state, the pump maintains a negative pressure for a specified time. This allows the clot to be affected by the pressure and break to thereby allow partial fluid flow or simply allow the clot to pass through the catheter. When the STATIC PLUG state has been active for less than a specified time, the Flow State is set to PLUG. If no changes occur to the clot, based on the pressure sensor values, then the Flow State switches to REMOVAL. During the PLUG Flow State, a change in the pressure can trigger a return back to the EXTRACT state. Once the Flow State has been set to REMOVAL, the algorithm maintains a static negative pressure until the start/stop button has been pressed.

The selected algorithm uses various pressure level values to control the pump operation. These include blood pressure (BP), upper positive pressure limit allowed by the pump BP (PUpper), lower negative pressure limit to trigger clot removal, and Atmospheric pressure (ATM).

The pump controller according to an embodiment of the invention keeps track of the total amount of time the unit has been ON and the time the current EXTRACT state has been active. These and other additional values can be stored with the processor for later retrieval.

Turning now to FIG. 11, a graphical representation displays the flow seen in a basic extraction where the clot was successfully removed with minimal issues. The process shown in FIG. 11 is detailed below.

Initially, the pump is in READY state (section A). Once the start/stop control) button is pressed, the pump aspirates (generated negative pressure) but this pressure drop is not low enough to indicate partial or full occlusion of the catheter, and therefore it is determined to be in the FREE FLOW state (section B). As soon as the catheter makes contact with the clot, a partial or full occlusion occurs and the pressure drops. This activates the EXTRACT state (section C).

During the EXTRACT state, the algorithm determines if positive or negative pressure is required to force the clot to degrade and go through the catheter. Once this occurs, the pressure increases and the pump returns to the FREE FLOW state (section D).

Once the start/stop button is again pressed, the pump stops and the pressure of the fluid returns to a stable value.

Referring to FIG. 12, a graph shown therein is directed to control of pump flow during a partial catheter occlusion. FIG. 12 displays a case in which the EXTRACT state is not able to remove the clot completely during a defined amount of time. The pump goes into the STATIC PLUG state and keeps a negative pressure, which can be seen when the pressure line drops towards a vacuum. If the occlusion can be removed at least partially, the pump changes to the EXTRACT state. This process is allowed to repeat until time limits are exceeded or used stops the process. The process shown in FIG. 12 is detailed below:

Initially the pump is in READY state (section A). Once the start/stop button is pressed, the pump aspirates (generates negative pressure). But this pressure drop is not low enough to indicate partial or full occlusion of the catheter, and therefore it is determined to be in the FREE FLOW state (section B).

As soon as the catheter makes contact with the clot, a partial or full occlusion occurs and the pressure drops. This activates the EXTRACT state (section C).

During the EXTRACT state, should the algorithm exceed a limit amount of time to remove the clot, the pump changes to the STATIC PLUG state and maintains a negative pressure. This can be seen when the pressure line drops towards vacuum (section D).

If the occlusion is partially removed, the pump switches back to the EXTRACT state and restarts the process (section E).

Once the clot is removed, the pump returns to the FREE FLOW state (section F), and eventually to the READY state once the start/stop button is pressed (not shown in FIG. 2).

Turning now to FIG. 13, the depicted graph shows pump flow during full occlusion. In the case that the EXTRACT state exceeds the defined time limit, the pump switches to the STATIC PLUG state. During this state, the pump aspirates, and keeps a negative pressure creating a vacuum. This state also has a time limit. The purpose is to simply force a constant negative pressure on the clot and extract the clot. This state can be switched back to the EXTRACT state if the pressure increases. This period is considered a “test” period. Once the time limit is exceeded the algorithm stops trying to remove the clot, and simply keeps the negative pressure while the user removes the catheter carefully along with the clot. Once this is done, the user presses the start/stop button to return the pump to the READY state. The process shown in FIG. 13 is detailed below.

Initially, the pump is in READY state (section A). Once the start/stop button is pressed, the pump aspirates (generated negative pressure) but this pressure drop is not low enough to indicate partial or full occlusion of the catheter therefore is determined to be in the FREE FLOW state (section B).

As soon as the catheter makes contact with the clot, a partial or full occlusion occurs and the pressure drops. This activates the EXTRACT state (section C). During the EXTRACT state, the algorithm has exceeded the limit amount of time (t1) to remove the clot. The pump changes to the STATIC PLUG state and maintains a negative pressure. This can be seen when the pressure line drops towards vacuum (section D).

The STATIC PLUG state also has a time limit (t2), which in FIG. 13 is shown to have been exceeded. This forces the pump to switch to terminate the algorithm and display a help screen for the user (section E).

Once the user removes the catheter with the clot, the start/stop button should be pressed to set the pump in READY state, in case an additional pass is required.

In order for the employed algorithm to switch from FREE FLOW state to the EXTRACT state, the pressure drops to a value defined by PLower. This drop triggers the change of state and the algorithm, based on the current pressure value, commands the pump to aspirate (generate a negative pressure) or infuse (generate a positive pressure).

The EXTRACT state starting time occurs when the first infuse command is made by the algorithm. The EXTRACT state has a time limit to prevent the algorithm from operating in a "forever" clot extraction mode.

Figure 14:
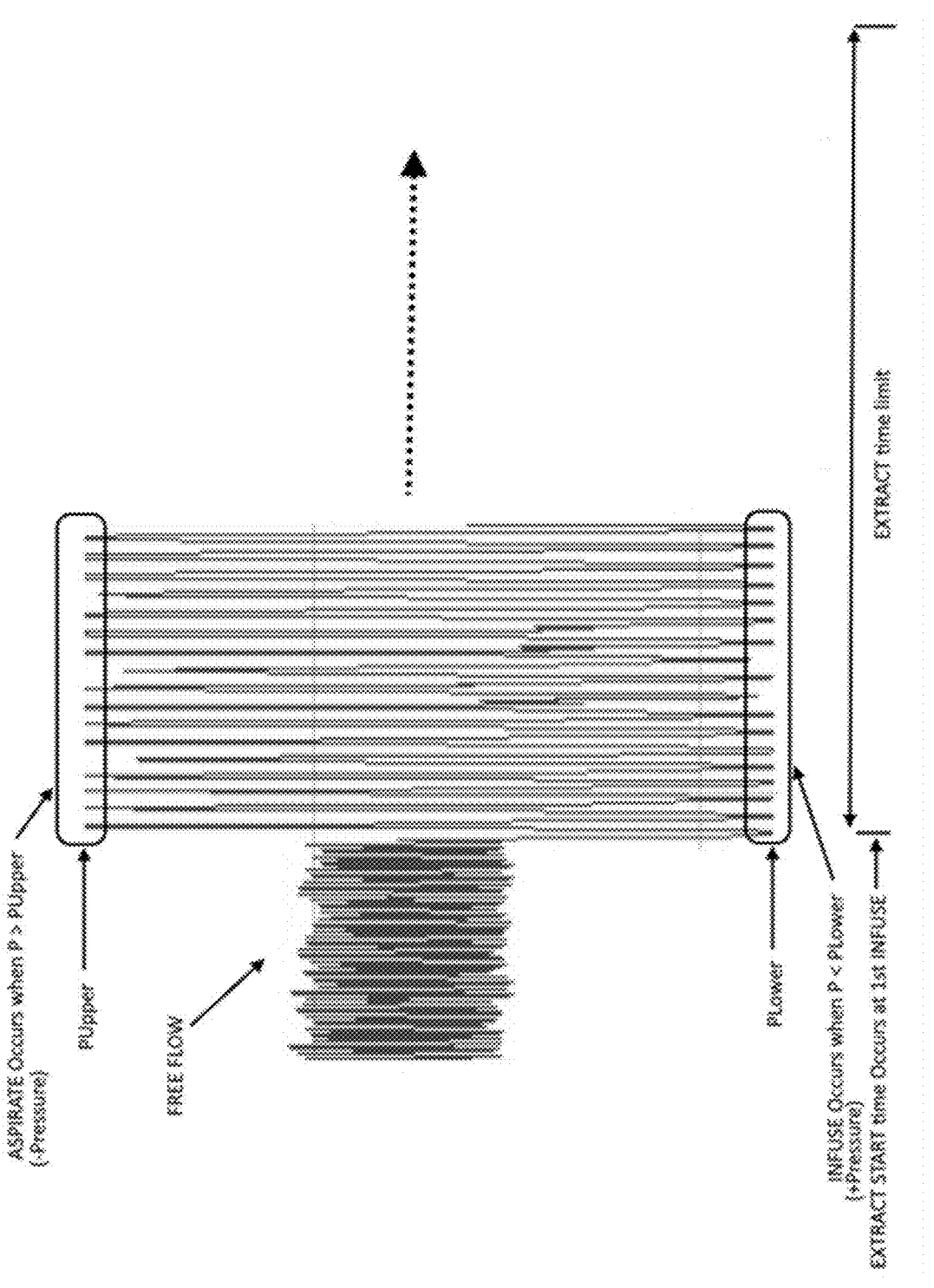
FIG. 14 is detailed graphical representation of pump flow stages associated with a start of the EXTRACT state.

FIG. 14 presents the various pressure levels and time limits defined in the algorithm.

In order to determine when the EXTRACT state is complete and the FREE FLOW state should be active, the algorithm looks at the timing in the infuse (+Pressure) commands.

In the previous section (6.0) the beginning of the EXTRACT state starts when the pressure drops to PLower and the timestamp for the start of the EXTRACT section occurs when the Infuse (+Pressure) command is generated by the algorithm. During the EXTRACT state, the algorithm will determine when the aspirate (–Pressure) and infuse (+Pressure) commands are required.

Figure 15:
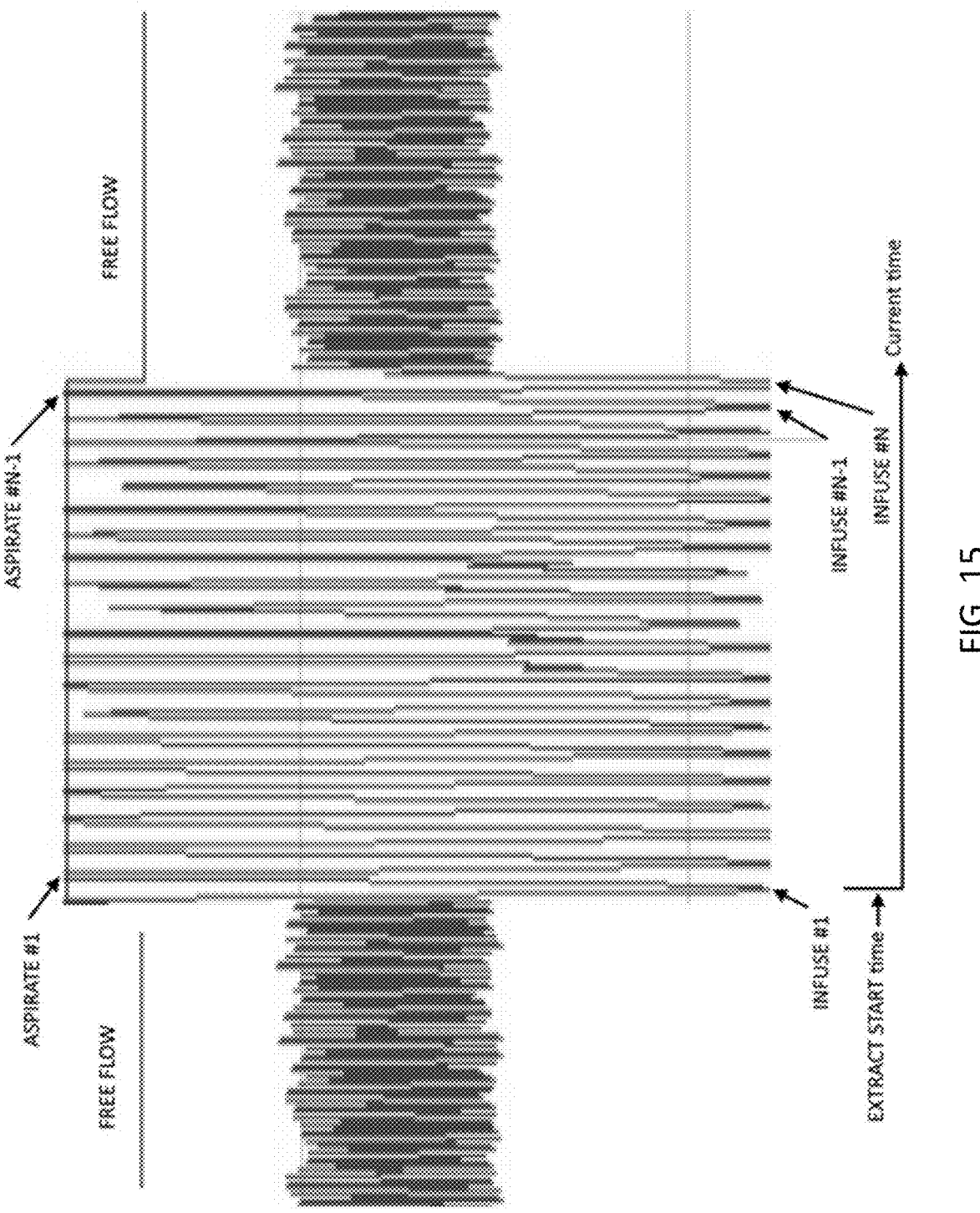
FIG. 15 is detailed graphical representation of associated with an end of the EXTRACT state.

FIG. 15 displays a detailed depiction at the end of the EXTRACT state when the aspirate and infuse commands are executed. In order for the infuse command to be executed, the pressure has to drop to PLower. If the pressure does not drop, this is an indication that the occlusion is minimal or none. The algorithm will remain aspirating. If the time between the current time and last time the infuse command was executed exceeds a time limit, then the algorithm sets the state to be FREE FLOW. In FREE FLOW the pump is continuously generating negative pressure. The user has to determine if there are additional clots or if all have been removed.

Figure 16:
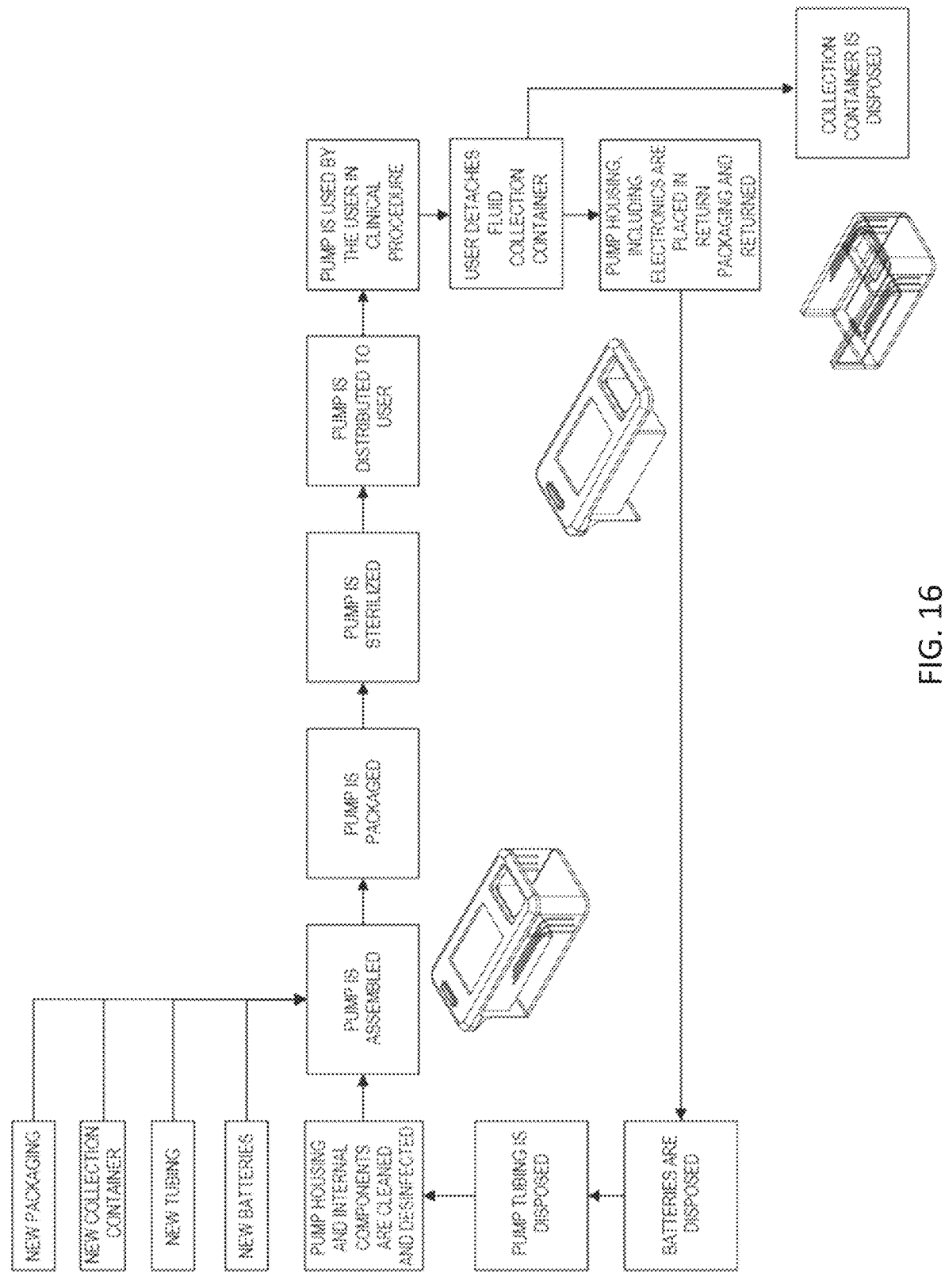
FIG. 16 is an annotated flow chart outlining a recycling and reprocessing model according to an exemplary embodiment of the invention.

FIG. 16 is an annotated flow chart outlining a recycling and reprocessing model according to an exemplary embodiment of the invention, setting forth an example of recycling methodologies according to one possible example of the invention.

FIGS. 17A and 17B illustrates in two views, a version of the system According to a particularly advantageous embodiment, clot capture device (Clot Catcher), fully integrated with the pump blood collection container, that allows the capture and immediate removal of the aspired clot without exiting the sterile field.

The Clot Catcher lid (see FIG. 17B) can be removed for collection of the extracted clot for subsequent examination and analysis. The clot catcher bottom is perforated as a sieve to allow the passage of blood while retaining the extracted clot.

The pump can also be operated with the cover of the clot catcher completely removed for even faster and easier clot removal by the user. All other conventional systems have their clot retrieval devices in line with the suction path. This requires the user to stop the pump to retrieve the clot. This means that clot retrieval from the catcher of other systems require the stoppage of the aspiration process to retrieve the clot. This invention beneficially allows the user to retrieve the extracted clot without stopping the aspiration process.

Figure 18:
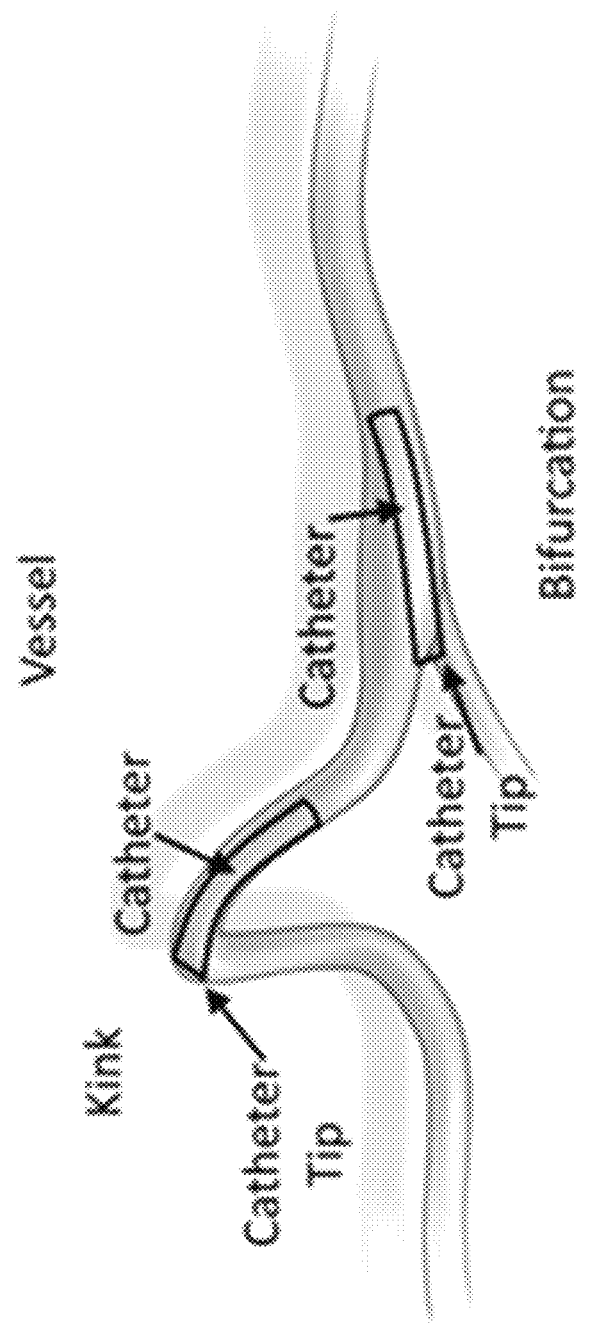
FIG. 18 is explanatory drawing outlining two cases of sidewall issues, including kink and bifurcation.

As depicted in FIG. 18, during a clot extraction procedure, a selected catheter is introduced within a vessel while aspirating. If the tip of the catheter is in contact with the wall of the vessel there are cases (sidewall) where the wall may cover the catheter tip as depicted in FIG. 18. As shown in the illustration, one possibility is an occurrence due to the catheter in contact with the vessel wall at a kink, and a second possibility is when the tip is located at a bifurcation. During any of these conditions, the pump pressure sensor immediately senses a drop in pressure (due to the momentary occlusion). Once the pressure drops below the lower pressure limit (PLower) this triggers the pump to start the extraction mode.

When the sidewall case occurs, the algorithm starts cycling between increasing and decreasing the pressure in the catheter. This has the effect of separating the catheter slightly from the vessel wall. At this point the algorithm senses a free flow condition (no occlusion due to a clot or to contact with a vessel wall). The state in the algorithm changes to FREE FLOW.

If the catheter due to the tortuosity of the vessel again is covered by the vessel wall this process of toggling between EXTRACTION and FREE FLOW modes will repeat itself many times.

At the algorithm level, the sidewall case consists of multiple toggles between the extracting and free flow modes. An EXTRACTING and then FREE FLOW state normally occurs when the aspiration system has removed the clot. This pair of states occur closely together but do not necessary repeat at short time intervals (as it occurs during a sidewall case).

The time interval between repeated EXTRACTING/ FREE FLOW states is compared against a time limit. Short intervals indicate a possible sidewall case is in effect. If the number of these events reaches an initial limit, a warning message is displayed suggesting that the catheter should be moved slightly to adjust the catheter tip location, thus removing the sidewall scenario. If a sidewall count variable exceeds a second limit then the pump is automatically switched to a STATIC pressure mode and a message is displayed indicating that the pump has been placed in STATIC pressure mode and that the catheter should be carefully retrieved. The static pressure will remain until the catheter is removed and the user presses a button indicating the process is complete. At this point all sidewall variables are reset and the pump is set to READY mode. At this point a new extraction process can be started.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention.

What is claimed is:

1. A method of aspirating a thrombus from a body lumen via a catheter coupled to a pump assembly, the pump assembly including a pump, the method comprising:

receiving at a controller an input associated with a catheter parameter associated with the catheter coupled to the pump assembly, the controller implemented in at least one of a memory or a processor coupled to the pump assembly;

selecting, via the controller, an aspiration algorithm associated with the catheter parameter, the aspiration algorithm including an upper pressure limit, a lower pressure limit, a clockwise speed, and a counter clockwise speed;

sending a first command to actuate the pump based on the aspiration algorithm to operate the pump in a first mode;

receiving at the controller a pressure signal associated with a catheter pressure from a sensor of the pump assembly; and sending, on a condition that the catheter pressure is below a pressure threshold, a second command to actuate the pump based on the aspiration algorithm to operate the pump in a second mode during which the pump is cycled between the clockwise speed and the counter clockwise speed such that the catheter pressure cycles between the upper pressure limit and the lower pressure limit.

2. The method of claim 1, further comprising:
receiving a user input associated with the catheter from a drop-down menu.

3. The method of claim 1, wherein the catheter parameter includes at least one of an inner diameter of the catheter, a compliance of the catheter, or a length of the catheter.

4. The method of claim 1, wherein the body lumen is a blood vessel, and the upper pressure limit is less than a blood pressure within the blood vessel.

5. The method of claim 1, wherein the first mode includes operating the pump at the clockwise speed.

6. The method of claim 5, further comprising:
after the sending the second command to actuate the pump to operate in a second mode, receiving at the controller a second pressure signal associated with a second catheter pressure from the sensor of the pump assembly; and
sending a notification to withdraw the catheter from the body lumen on a condition that the second catheter pressure is below a preset pressure limitation indicating a plugged state.

7. The method of claim 1, further comprising:
sending a notification to withdraw the catheter from the body lumen on a condition that a time period of operating the pump in the second mode has exceeded a time threshold thereby indicating a plugged state.

8. The method of claim 1, further comprising:
after the sending the second command to actuate the pump to operate the pump in the second mode, receiving a second pressure signal associated with a second catheter pressure from the sensor of the pump assembly; and
sending a third command to actuate the pump to operate the pump in a third mode based on the selected aspiration algorithm, the third mode includes operating the pump at the clockwise speed.

9. An apparatus, comprising:
a thrombectomy pump assembly disposed within a housing, the thrombectomy pump assembly including a pump, the thrombectomy pump assembly configured to aspirate a thrombus from a body lumen via a catheter coupled to the pump;
a display coupled to the housing; and
a controller coupled within the housing, the controller including at least one of a memory or a processor, the controller configured to:
(1) receive a first input, the first input associated with a catheter parameter associated with a catheter to be coupled to the pump assembly, (2) select an aspiration algorithm associated with the catheter parameter, the aspiration algorithm including an upper pressure limit, a lower pressure limit, a clockwise speed, and a counter clockwise speed, (3) send a command based on the aspiration algorithm to the thrombectomy pump assembly to operate the thrombectomy pump assembly in a first mode, (4) receive a pressure signal associated with a catheter pressure from a sensor of the thrombectomy pump assembly, and (5) send a second command based on the aspiration algorithm to the thrombectomy pump assembly to operate the thrombectomy pump assembly in a second mode during which the pump is cycled between the clockwise speed and the counter clockwise speed such that the catheter pressure cycles between the upper pressure limit and the lower pressure limit.

10. The apparatus of claim 9, wherein the catheter parameter includes at least one of an inner diameter of the catheter, a compliance of the catheter, or a length of the catheter.

11. The apparatus of claim 9, wherein the body lumen is a blood vessel, and the upper pressure limit is less than a blood pressure within the blood vessel.

12. The apparatus of claim 9, wherein the first mode includes operating the pump at the clockwise speed.

13. The apparatus of claim 12, wherein the controller is further configured to:
receive, after the sending the second command to the pump assembly to operate the pump in the second mode, a second pressure signal associated with a second catheter pressure from the sensor of the pump assembly; and
send a notification to withdraw the catheter from the body lumen on a condition that the pressure is below a preset pressure limitation indicating a plugged state.

14. The apparatus of claim 9, wherein the controller is further configured to:
send a notification to withdraw the catheter from the body lumen on a condition that a time period of operating the pump in the second mode has exceeded a time threshold thereby indicating a plugged state.

15. The apparatus of claim 9, wherein the controller is further configured to:
receive, after the sending the second command to the pump assembly to operate the pump assembly in the second mode, a second pressure signal associated with a second catheter pressure from the sensor of the pump assembly; and
send a third command to the pump assembly to operate the pump assembly in a third mode based on the selected aspiration algorithm, the third mode includes operating the pump at the clockwise speed.

16. A method of removing a thrombus from a body lumen via a catheter coupled to a pump assembly, the pump assembly including a pump, the method comprising:
selecting, via a controller, an aspiration algorithm including an upper pressure limit, a lower pressure limit, a clockwise speed, and a counter clockwise speed;
sending via the controller, a first command to the pump assembly to operate the pump assembly in a first mode based on the aspiration algorithm, the first mode including operating the pump at the clockwise speed;
receiving a first pressure signal associated with a catheter pressure from a sensor of the pump assembly;
sending via the controller in response to the first pressure signal, a second command to the pump assembly to operate the pump assembly in a second mode based on the aspiration algorithm during which the pump is cycled between the clockwise speed and the counter clockwise speed such that the catheter pressure cycles between the upper pressure limit and the lower pressure limit;
receiving at the controller a second pressure signal associated with a second catheter pressure from the sensor of the pump assembly; and
sending via the controller in response to the second pressure signal a third command to the pump assembly to operate the pump assembly in a third mode based on the aspiration algorithm, the third mode including operating the pump at the clockwise speed.

17. The method of claim 16, further comprising:
after the receiving the second pressure signal associated
with the second catheter pressure from the sensor of the
pump assembly, sending a notification to withdraw the
catheter from the body lumen if the second catheter    5
pressure is below a preset pressure limitation indicating
a plugged state.

\*    \*    \*    \*    \*